US011208527B2

(12) United States Patent
Easwaran et al.

(10) Patent No.: US 11,208,527 B2
(45) Date of Patent: Dec. 28, 2021

(54) PHOTOACTIVE MACROMOLECULES AND USES THEREOF

(71) Applicant: Beckman Coulter, Inc., Brea, CA (US)

(72) Inventors: Arunkumar Easwaran, Miami, FL (US); Sergei Gulnik, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 227 days.

(21) Appl. No.: 16/092,180

(22) PCT Filed: Apr. 14, 2017

(86) PCT No.: PCT/US2017/027611
§ 371 (c)(1),
(2) Date: Oct. 8, 2018

(87) PCT Pub. No.: WO2017/180998
PCT Pub. Date: Oct. 19, 2017

(65) Prior Publication Data
US 2019/0144601 A1    May 16, 2019

Related U.S. Application Data

(60) Provisional application No. 62/323,444, filed on Apr. 15, 2016.

(51) Int. Cl.
| | |
|---|---|
| *C08G 61/02* | (2006.01) |
| *G01N 33/533* | (2006.01) |
| *C08G 61/12* | (2006.01) |
| *G01N 33/58* | (2006.01) |
| *C09K 11/06* | (2006.01) |

(52) U.S. Cl.
CPC .......... *C08G 61/126* (2013.01); *C08G 61/02* (2013.01); *C08G 61/124* (2013.01); *C09K 11/06* (2013.01); *G01N 33/533* (2013.01); *G01N 33/582* (2013.01); *C08G 2261/12* (2013.01); *C08G 2261/145* (2013.01); *C08G 2261/1424* (2013.01); *C08G 2261/1644* (2013.01); *C08G 2261/3142* (2013.01); *C08G 2261/3327* (2013.01); *C08G 2261/342* (2013.01); *C08G 2261/411* (2013.01); *C08G 2261/522* (2013.01); *C08G 2261/94* (2013.01)

(58) Field of Classification Search
CPC .............. C08G 61/02; C08G 2261/145; C08G 2161/1644; C08G 2261/3142; C08G 2261/1644; C08G 2261/3327; C08G 2261/342; C08G 2261/94; C08G 61/126; G01N 33/533; G01N 33/582
See application file for complete search history.

(56) References Cited

U.S. PATENT DOCUMENTS

| | | |
|---|---|---|
| 4,486,530 A | 12/1984 | David et al. |
| 4,703,004 A | 10/1987 | Hopp et al. |
| 5,187,288 A | 2/1993 | Kang et al. |
| 5,573,909 A | 11/1996 | Singer et al. |
| 5,576,424 A | 11/1996 | Mao et al. |
| 5,582,977 A | 12/1996 | Yue et al. |
| 5,656,449 A | 8/1997 | Yue |
| 5,658,751 A | 8/1997 | Yue et al. |
| 5,696,157 A | 12/1997 | Wang et al. |
| 5,723,218 A | 3/1998 | Haugland et al. |
| 5,798,276 A | 8/1998 | Haugland et al. |
| 5,846,737 A | 12/1998 | Kang |
| 5,863,753 A | 1/1999 | Haugland et al. |
| 6,004,536 A | 12/1999 | Leung et al. |
| 6,005,113 A | 12/1999 | Wu et al. |
| 6,130,101 A | 10/2000 | Mao et al. |
| 6,162,931 A | 12/2000 | Gee et al. |
| 6,316,267 B1 | 11/2001 | Bhalgat et al. |
| 6,399,392 B1 | 6/2002 | Haugland et al. |
| 6,562,632 B1 | 5/2003 | Szalecki et al. |
| 6,579,718 B1 | 6/2003 | Yue et al. |
| 6,716,979 B2 | 4/2004 | Diwu et al. |
| 6,972,326 B2 | 12/2005 | Haugland et al. |
| 7,144,950 B2 | 12/2006 | Bazan et al. |
| 7,446,202 B2 | 11/2008 | Dallwig et al. |
| 7,462,683 B2 | 12/2008 | Yamamoto et al. |
| 7,666,392 B2 | 2/2010 | Kolb et al. |
| 7,671,214 B2 | 3/2010 | Leung et al. |
| 7,687,282 B2 | 3/2010 | Tsien et al. |
| 7,723,455 B2 | 5/2010 | Becker et al. |
| 7,855,275 B2 | 12/2010 | Eigenbrot et al. |
| 8,309,300 B2 | 11/2012 | Junutula et al. |
| 8,362,193 B2 | 1/2013 | Gaylord et al. |

(Continued)

FOREIGN PATENT DOCUMENTS

| | | |
|---|---|---|
| AU | 2017250778 A1 | 11/2018 |
| BR | 112018071026 A2 | 2/2019 |

(Continued)

OTHER PUBLICATIONS

Chen et al. Journal of Polymer Science, Part A: Polymer Chemistry (2009), 47(19), 5057-5067 (Year: 2009).*
"Australian Application Serial No. 2017250778, First Examination Report dated Oct. 9, 2020", 4 pgs.
"Brazilian Application Serial No. 1120180710261, Voluntary Amendment filed Apr. 8, 2020", w/English claims, 36 pgs.
"European Application Serial No. 17737077.2, Response filed May 23, 2019 to Communication pursuant to Rules 161(1) and 162 EPC dated Nov. 22, 2018", 29 pgs.

(Continued)

*Primary Examiner* — Jezia Riley
(74) *Attorney, Agent, or Firm* — Schwegman Lundberg & Woessner, P.A.

(57) ABSTRACT

The present invention provides water soluble photoactive macromolecular complexes and methods for detecting an analyte in a sample by using a binding agent conjugated to a water soluble photoactive macromolecule.

22 Claims, 5 Drawing Sheets

(56) References Cited

U.S. PATENT DOCUMENTS

| | | | |
|---|---|---|---|
| 8,455,613 | B2 | 6/2013 | Gaylord et al. |
| 8,575,303 | B2 | 11/2013 | Gaylord et al. |
| 9,000,130 | B2 | 4/2015 | Bhakta et al. |
| 9,139,869 | B2 | 9/2015 | Gaylord et al. |
| 9,547,008 | B2 | 1/2017 | Gaylord et al. |
| 9,896,538 | B2 | 2/2018 | Diwu et al. |
| 10,094,838 | B2 | 10/2018 | Gaylord et al. |
| 10,288,620 | B2 | 5/2019 | Gaylord et al. |
| 10,302,648 | B2 | 5/2019 | Gaylord et al. |
| 10,365,285 | B2 | 7/2019 | Gaylord et al. |
| 10,458,989 | B2 | 10/2019 | Gaylord et al. |
| 10,641,775 | B2 | 5/2020 | Gaylord et al. |
| 10,955,417 | B2 | 3/2021 | Gaylord et al. |
| 10,962,546 | B2 | 3/2021 | Gaylord et al. |
| 2004/0101909 | A1 | 5/2004 | Lemieux et al. |
| 2005/0059168 | A1 | 3/2005 | Bazan et al. |
| 2006/0183140 | A1 | 8/2006 | Bazan et al. |
| 2007/0060736 | A1 | 3/2007 | Becker et al. |
| 2010/0150942 | A1 | 6/2010 | Cantor |
| 2010/0227974 | A1 | 9/2010 | Schulte et al. |
| 2011/0095280 | A1 | 4/2011 | Meyer et al. |
| 2011/0256549 | A1* | 10/2011 | Gaylord .................. C09B 69/00 435/7.1 |
| 2013/0011388 | A1 | 1/2013 | Nur et al. |
| 2013/0027636 | A1 | 1/2013 | Marrocco, III et al. |
| 2013/0108619 | A1 | 5/2013 | Melamed |
| 2013/0177574 | A1 | 7/2013 | Ravindranath et al. |
| 2014/0357898 | A1 | 12/2014 | Kawano et al. |
| 2020/0190253 | A1 | 6/2020 | Easwaran et al. |

FOREIGN PATENT DOCUMENTS

| | | | |
|---|---|---|---|
| BR | 102019025989 | A2 | 6/2020 |
| CA | 3020926 | A1 | 10/2017 |
| CN | 109415623 | A | 3/2019 |
| CN | 111320744 | A | 6/2020 |
| EP | 1717258 | A1 | 11/2006 |
| EP | 3443049 | A2 | 2/2019 |
| EP | 3670609 | A1 | 6/2020 |
| EP | 3443049 | B1 | 4/2021 |
| JP | 2008519140 | A | 6/2008 |
| JP | 2010501030 | A | 1/2010 |
| JP | 2010503685 | A | 2/2010 |
| JP | 2011500916 | A | 1/2011 |
| JP | 2019519623 | A | 7/2019 |
| JP | 2020109162 | A | 7/2020 |
| JP | 6882331 | B2 | 5/2021 |
| JP | 2021102779 | A | 7/2021 |
| JP | 2021165407 | A | 10/2021 |
| KR | 20180132750 | A | 12/2018 |
| WO | WO-2005014689 | A2 | 2/2005 |
| WO | WO-2005100437 | A1 | 10/2005 |
| WO | 2008100344 | A2 | 8/2008 |
| WO | WO-2009051560 | A1 | 4/2009 |
| WO | 2010151807 | A1 | 12/2010 |
| WO | 2011091086 | A1 | 7/2011 |
| WO | WO-2016019929 | A2 | 2/2016 |
| WO | WO-2016144653 | A1 | 9/2016 |
| WO | WO-2017180998 | A2 | 10/2017 |
| WO | WO-2017180998 | A3 | 12/2017 |

OTHER PUBLICATIONS

"European Application Serial No. 19216268.3, Extended European Search Report dated May 26, 2020", 7 pgs.
"Indian Application Serial No. 201847039964, First Examination Report dated Jul. 7, 2020", w/English Translation, 6 pgs.
"International Application Serial No. PCT/US2017/027611, International Preliminary Report on Patentability dated Oct. 25, 2018", 10 pgs.
PCT/US2017/027611, "International Search Report and Written Opinion", dated Dec. 7, 2017, 17 pages.
PCT/US2017/027611, "Invitation to Pay Add'l Fees and Partial Search Report", dated Oct. 11, 2017, 10 pages.
Yamamoto et al. "π-Conjugated Polymers Consisting of 9,10-Dihydrophenanthrene Units" Macromol. Chem. Phys. 2011, vol. 212, pp. 2406-2416.
"Australian Application Serial No. 2017250778, Response filed Aug. 4, 2021 to First Examination Report dated Oct. 9, 2021", 35 pgs.
"Australian Application Serial No. 2019280076, First Examination Report dated Jun. 18, 2021", 3 pgs.
"Becton Dickinson Filed a Case Against Beckman Coulter Over Alleged Patent Infringement", MaxVal, [Online] Retrieved from the Internet: <URL: https://www.maxval.com/blog/becton-dickinson-filed-a-case-against-beckman-coulter-over-alleged-patent-infringement/>, [Retrieved on Sep. 29, 2021], (Jul. 1, 2021), 6 pgs.
"Brazilian Application Serial No. 1120180710261, Office Action dated Jun. 1, 2021", w/ English Machine Translation, 10 pgs.
"Brazilian Application Serial No. 1120180710261, Office Action dated Aug. 13, 2021", w/ English Claims, 80 pgs.
"Chinese Application Serial No. 201780031306.5, Office Action dated May 8, 2021", w/ English Translation, 32 pgs.
"Chinese Application Serial No. 201780031306.5, Response filed Aug. 17, 2021 to Office Action dated May 8, 2021", w/o English Claims, 34 pgs.
"European Application Serial No. 17737077.2, Intention to Grant a European Patent dated Mar. 18, 2021", w/ Allowed Claims, 12 pgs.
"European Application Serial No. 19216268.3, Response filed Dec. 18, 2020 to Extended European Search Report dated May 26, 2020", 15 pgs.
"European Application Serial No. 21156248.3, Response to Rule 58 filed Apr. 28, 2021", 12 pgs.
"Indian Application Serial No. 201847039964, Hearing Notice dated Jan. 1, 2021", 2 pgs.
"Indian Application Serial No. 201847039964, Response filed Dec. 24, 2020 to First Examination Report, dated Jul. 7, 2020", 44 pgs.
"Japanese Application Serial No. 2018-554032, Decision to Grant a Patent dated Apr. 26, 2021", w/ English Translation and Allowed Claims, 22 pgs.
"Japanese Application Serial No. 2018-554032, Notification of Reasons for Rejection dated Jan. 15, 2021", w/ English Translation, 9 pgs.
"Japanese Application Serial No. 2018-554032, Response filed Apr. 2, 2021 to Office Action dated Jan. 15, 2021", w/ English Translation, 56 pgs.
"Japanese Application Serial No. 2021-63576, Voluntary Amendment filed Jul. 14, 2021", w/ English claims, 24 pgs.
"Korean Application Serial No. 10-2018-7031258, Notice of Allowance dated Aug. 23, 2021", w/ English Translation, 4 pgs .
"Korean Application Serial No. 10-2018-7031258, Notice of Preliminary Rejection dated Mar. 11, 2021", w/ English Translation, 17 pgs.
"Korean Application Serial No. 10-2018-7031258, Response filed May 11, 2021 to Notice of Preliminary Rejection dated Mar. 11, 2021", w/ English claims, 64 pgs.
An, Lingling, et al., "A Fluorescence Ratiometric Protein Assay Using Light-Harvesting Conjugated Polymers", Macromol. Rapid Commun. 2006, 27, (2006), 993-997.
An, Lingling, et al., "Cationic conjugated polymers for homogeneous and sensitive fluorescence detection of hyaluronidase", Sci China Ser B-Chem, 52(6), (Jun. 2009), 827-832.
Bernius, Mark T, et al., "Progress with Light-Emitting Polymers", Adv. Mater. 2000, 12(23), (Dec. 1, 2000), 1737-1750.
Burrows, Hugh D, et al., "Aqueous Solution Behavior of Anionic Fluorene-co-thiophene-Based Conjugated Polyelectrolytes", Applied Materials and Interfaces, 1(4), (2009), 864-874.
Feng, Fude, et al., "Water-Soluble Conjugated Polymers for Fluorescent-Enzyme Assays", Macromol. Rapid Commun. 2010, 31, (2010), 1405-1421.
Gaylord, Brent S, et al., "DNA detection using water-soluble conjugated polymers and peptide nucleic acid probes", PNAS, 99(17), (2002), 10954-10957.
Gaylord, Brent, et al., "DNA Hybridization Detection with Water-Soluble Conjugated Polymers and Chromophore-Labeled Single-Stranded DNA", J. Am. Chem. Soc., 125(4), (2003), 896-900.

(56) References Cited

OTHER PUBLICATIONS

Gaylord, Brent S, et al., "SNP detection using peptide nucleic acid probes and conjugated polymers: Applications in neurodegenerative disease identification", PNAS, 102(1), (Jan. 4, 2005), 34-39.

Hou, Qiong, et al., "Novel red-emitting fluorene-based copolymers", J. Mater. Chem., 2002, 12, (2002), 2887-2892.

Inbasekaran, Michael, et al., "Fluorene homopolymers and copolymers", Synthetic Metals 111-112, (2000), 397-401.

Lee, Kangwon, et al., "Sensitive and Selective Label-Free DNA Detection by Conjugated Polymer-Based Microarrays and Intercalating Dye", Chem. Mater. 2008, 20(9), (2008), 2848-2850.

Li, Kai, et al., "Generic Strategy of Preparing Fluorescent Conjugated-Polymer-Loaded Poly(DL-lactide-co-Glycolide) Nanoparticles for Targeted Cell Imaging", Adv. Funct. Mater. 2009, 19, (2009), 3535-3542.

Li, Kai, et al., "Water-soluble conjugated polymers as the platform for protein sensors", Polym. Chem., 2010, 1., (2010), 252-259.

Liu, Bin, et al., "Synthesis of a novel cationic water-soluble efficient blue photoluminescent conjugated polymer", Chem. Commun., 2000, (2000), 551-552.

Liu, Bin, et al., "Synthesis of cationic conjugated polymers for use in label-free DNA microarrays", Nature Protocols, 1(4), (2006), 1698-1702.

Pei, Qibing, et al., "Efficient Photoluminescence and Electroluminescence from a Soluble Polyfluorene", J. Am. Chem. Soc. 1996, 118, (1996), 7416-7417.

Pu, Fang, et al., "Universal Platform for Sensitive and Label-Free Nuclease Assay Based on Conjugated Polymer and DNA/Intercalating Dye Complex", Langmuir 2010, 26(6), (2010), 4540-4545.

Shi, Jianbing, et al., "Synthesis and Characterization of Water-Soluble Conjugated Glycopolymer for Fluorescent Sensing of Concanavalin A", Chem. Asian J. 2010, 5, (2010), 301-308.

Stork, Martin, et al., "Energy Transfer in Mixtures of Water-Soluble Oligomers: Effect of Charge, Aggregation, and Surfactant Complexation", Adv. Mater. 2002, 14(5), (Mar. 4, 2002), 361-366.

Sun, Chengjun, et al., "Application of cationic conjugated polymers in microarrays using label-free DNA targets", Nature Protocols, 2(9), (2007), 2148-2151.

Wang, Shu, et al., "Fluorescein Provides a Resonance Gate for FRET from Conjugated Polymers to DNA Intercalated Dyes", J. Am. Chem. Soc., 126(17), (2004), 5446-5451.

Xue, Cuihua, et al., "Facile, Versatile Prepolymerization and Postpolymerization Functionalization Approaches for Well-Defined Fluorescent Conjugated Fluorene-Based Glycopolymers", Macromolecules 2006, 39, (2006), 5747-5752.

Xue, Cuihua, et al., "Highly Water-Soluble, Fluorescent, Conjugated Fluorene-Based Glycopolymers with Poly(ethylene glycol)-Tethered Spacers for Sensitive Detection of *Escherichia coli*", Chem. Eur. J. 2009, 15, (2009), 2289-2295.

"European Application Serial No. 21156248.3, Extended European Search Report dated Oct. 8, 2021", 5 pgs.

Yamamoto, T, et al., "Synthesis of soluble poly(9,10-dihydrophenanthrene-2,7-diyl)s.A new class of luminescent poly(p-phenylene)s with ethylene type bridges", Polymer, Elsevier Science Publishers B.V, GB, vol. 45, No. 24, (Nov. 1, 2004), 8085-8089.

\* cited by examiner

| Abs/Em Max | MW ($M_n$) | PD | $\varepsilon$ | $\phi$ | Brightness | F/P |
|---|---|---|---|---|---|---|
| $\lambda_{max}$ 395-415 nm $\lambda_{em}$ 420-430 nm | 20K-70K | Between 1.5 to 2.5 | 300K to 2500K | 0.4 to 0.75 | 150K to 1900K | 1 to 12 |
| $\lambda_{max}$ 340-370 nm $\lambda_{em}$ 390-420 nm | 20K-70K | Between 1.5 to 2.5 | 300K to 2500K | 0.1 to 0.75 | 30K to 1900K | 1 to 12 |

FIG. 4

PHOTOACTIVE MACROMOLECULES AND USES THEREOF

CROSS-REFERENCES TO RELATED APPLICATIONS

This application claims priority to U.S. Provisional Application No. 62/323,444, filed on Apr. 15, 2016, the contents of which are incorporated by reference herewith in their entirety.

FIELD OF THE INVENTION

This invention relates to complexes and methods for detecting analytes in a sample.

BACKGROUND OF THE INVENTION

Water soluble fluorescent polymers can be used in a variety of biological applications by generating signals which can be monitored in real time and provide simple and rapid methods for the detection of biological targets and events.

Brightness of a dye is an overall contribution from the extinction coefficient (ε, measure of the amount of light absorbed at a particular wavelength) and fluorescence quantum yield (Φ, measure of the light emitted in the form of radiation from its singlet excited state). Most of the reported organic violet dyes such as coumarin, BODIPY, cyanine, squaraine etc are single molecules and shows relatively low extinction coefficient in the range of 10,000-70,000 $M^{-1}cm^{-1}$ at 405 nm. It has been shown that molecules having multiple chromophores exhibit higher ε value due to the overall contribution from different chromophores. There are various reports on dendrimeric and polymeric backbone approaches where a single molecule contains multiple chromophores.

However, many of the previously reported polymeric dyes are highly hydrophobic and are used for material applications such as light emitting diodes, solar cells etc. Consequently, many polymeric dyes are not useful under aqueous conditions due to the poor solubility, brightness, and broadening of the spectra. Only a few reports deal with water soluble fluorescent polymers for biological applications which are excitable with a 405 nm and 355 nm laser. Therefore, identification of novel polymeric cores is needed in order to expand the arsenal of water soluble polymeric dyes for biological applications, including for the detection of analytes.

The present invention addresses these and other disadvantages of prior art complexes and methods for detecting analytes in a sample.

BRIEF SUMMARY OF THE INVENTION

The present invention generally provides novel, water soluble fluorescent polymers and methods for detecting analytes in a sample using complexes comprising the fluorescent polymers conjugated to binding agents.

In a first embodiment, the present invention provides a water soluble fluorescent polymer having the structure of Formula I:

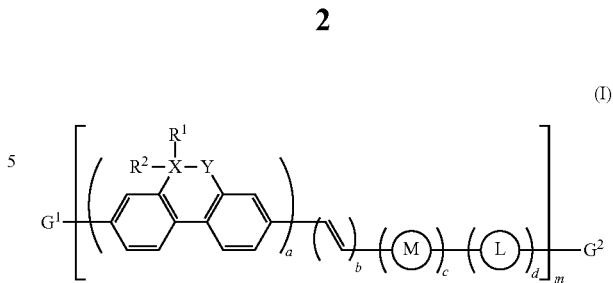

wherein;

each X is independently selected from the group consisting of a C and Si;

each Y is independently selected from the group consisting of a bond, $CR^1R^2$, and $SiR^1R^2$;

when Y is a bond X is directly bonded to both rings;

each $R^1$ is independently selected from the group consisting of polyethylene glycol (PEG), ammonium alkyl salt, ammonium alkyloxy salt, ammonium oligoether salt, sulfonate alkyl salt, sulfonate alkoxy salt, sulfonate oligoether salt, sulfonamido oligoether, and

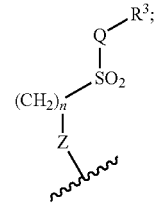

each $R^2$ is independently selected from the group consisting of H, alkyl, alkene, alkyne, cycloalkyl, haloalkyl, alkoxy, (hetero)aryloxy, aryl, (hetero)arylamino, PEG, ammonium alkyl salt, ammonium alkyloxy salt, ammonium oligoether salt, sulfonate alkyl salt, sulfonate alkoxy salt, sulfonate oligoether salt, sulfonamido oligoether, and

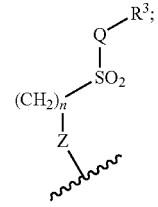

each $R^3$ is independently selected from the group consisting of H, alkyl, alkene, alkyne, cycloalkyl, haloalkyl, alkoxy, (hetero)aryloxy, aryl, (hetero)arylamino, and PEG;

each Z is independently selected from the group consisting of C, O, and N;

each Q is independently selected from the group consisting of a bond, NH, $NR^4$, and $CH_2$;

each M is independently an electron rich linker unit capable of altering the polymer band gap and is evenly or randomly distributed along the polymer main chain and is each independently selected from the group consisting of

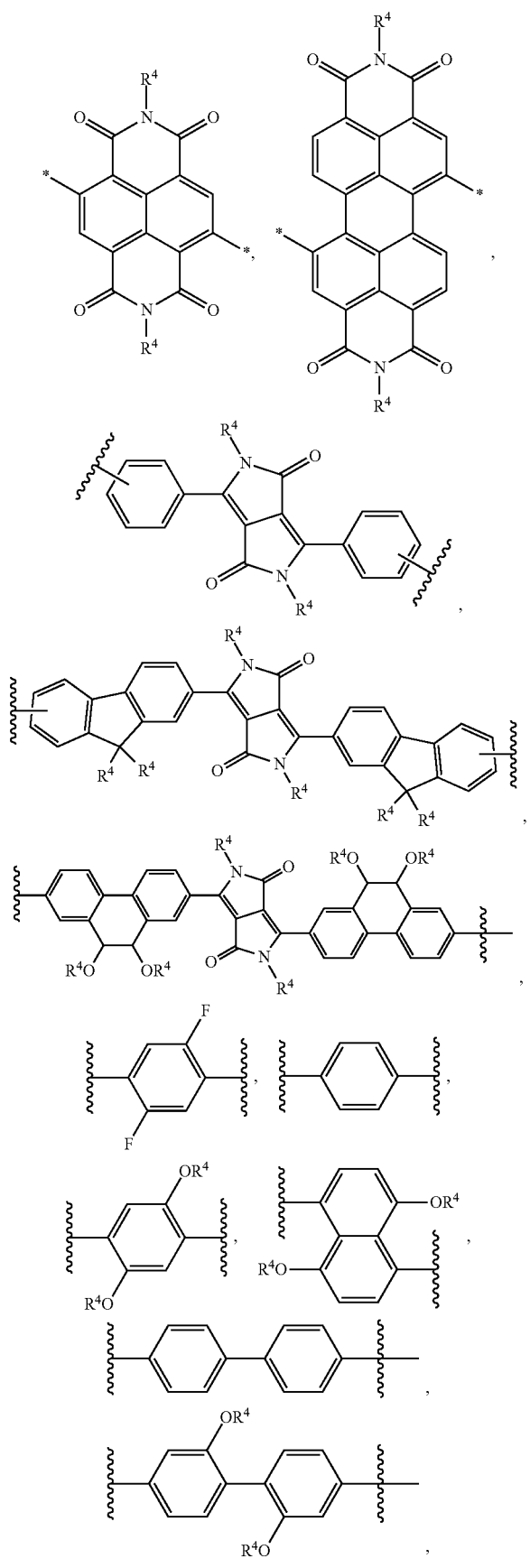

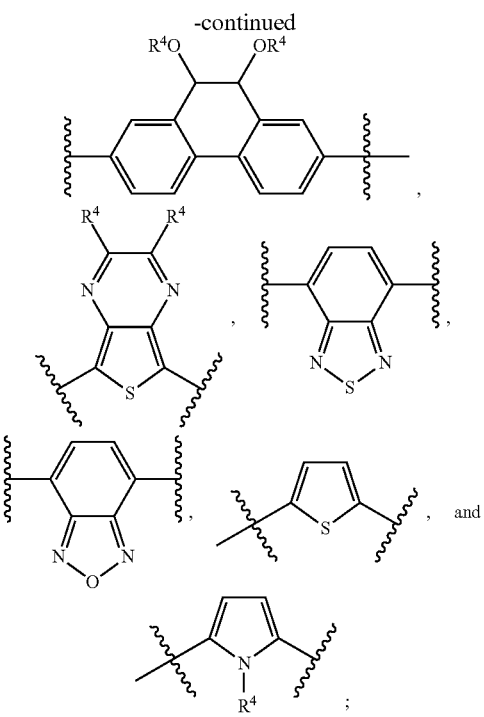

wherein, each $R^4$ is a non-ionic side group capable of imparting solubility in water in excess if 10 mg/mL and is each independently selected from the group consisting of halogen, hydroxyl, $C_1$-$C_{12}$ alkyl, $C_2$-$C_{12}$ alkene, $C_2$-$C_{12}$ alkyne, $C_3$-$C_{12}$ cycloalkyl, $C_1$-$C_{12}$ haloalkyl, $C_1$-$C_{12}$ alkoxy, $C_2$-$C_{18}$ (hetero)aryloxy, $C_2$-$C_{18}$ (hetero)arylamino, $(CH_2)_{x'}(OCH_2$—$CH_2)_{y'}OCH_3$ where each x' is independently an integer from 0-20; each y' is independently an integer from 0-50, and a $C_2$-$C_{18}$ (hetero) aryl group;

each optional linker L is an aryl or hetroaryl group evenly or randomly distributed along the polymer main chain and are substituted with one or more pendant chains terminated with a functional group selected from the group consisting of amine, carbamate, carboxylic acid, carboxylate, maleimide, activated ester, N-hydroxysuccinimidyl, hydrazine, hydrazide, hydrazone, azide, alkyne, aldehyde, thiol, and protected groups thereof for conjugation to another substrate, acceptor dye, molecule or binding agent;

each $G^1$ and $G^2$ are each independently selected from the group consisting of hydrogen, halogen, alkyne, optionally substituted aryl, optionally substituted heteroaryl, halogen substituted aryl, silyl, diazonium salt, triflate, acetyloxy, azide, sulfonate, phosphate, boronic acid substituted aryl, boronic ester substituted aryl, boronic ester, boronic acid, optionally substituted dihydrophenanthrene (DHP), optionally substituted fluorene, aryl or hetroaryl substituted with one or more pendant chains terminated with a functional group selected from amine, carbamate, carboxylic acid, carboxylate, maleimide, activated ester, N-hydroxysuccinimidyl, hydrazine, hydrazide, hydrazone, azide, alkyne, aldehyde, thiol, and protected groups thereof for conjugation to a substrate or a binding agent;

a, c, and d, define the mol % of each unit within the structure which each can be evenly or randomly repeated and where a is a mol % from 10 to 100%, c is a mol % from 0 to 90%, and each d is a mol % from 0 to 25%;

each b is independently 0 or 1;

m is an integer from 1 to about 10,000; and each n is independently an integer from 1 to 20.

In some cases, the polymer has the structure of Formula II:

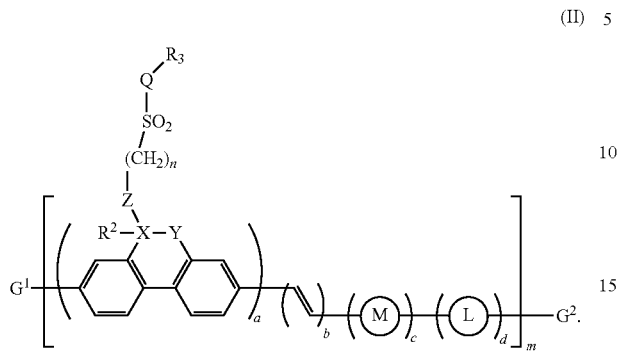

(II)

In some cases, the polymer has the structure of Formula III:

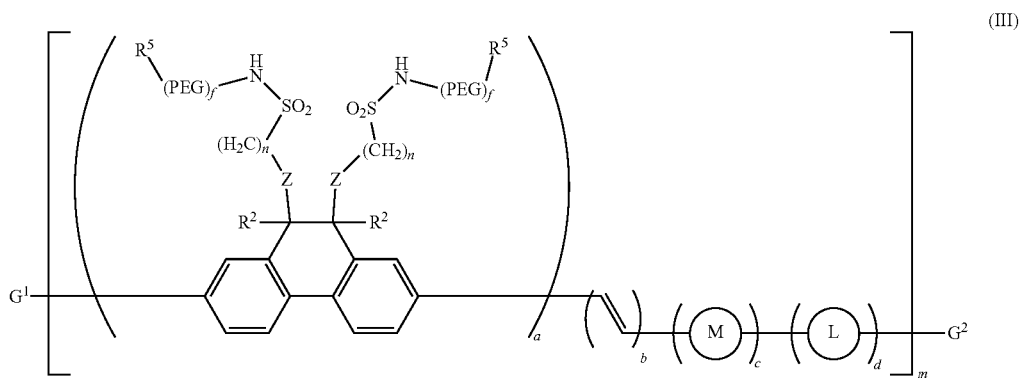

(III)

wherein, each f is independently an integer from 0 to 50 and each $R^5$ is independently selected from the group consisting of H, $C_1$-$C_{12}$ alkyl, $C_2$-$C_{12}$ alkene, $C_2$-$C_{12}$ alkyne, $C_3$-$C_{12}$ cycloalkyl, $C_1$-$C_{12}$ haloalkyl, $C_1$-$C_{12}$ alkoxy, $C_2$-$C_{18}$ (hetero)aryloxy, $C_2$-$C_{18}$ (hetero)arylamino, and $C_1$-$C_{12}$ alkoxy.

In some cases the polymer has the structure of Formula IV:

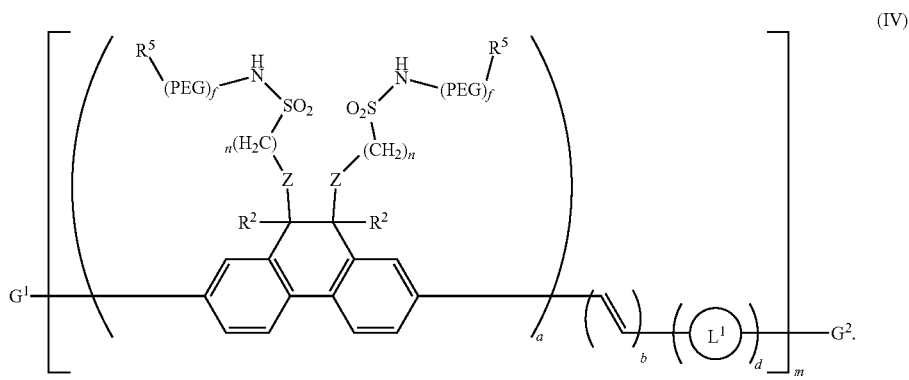

(IV)

In some cases, the polymer has the structure of Formula V:

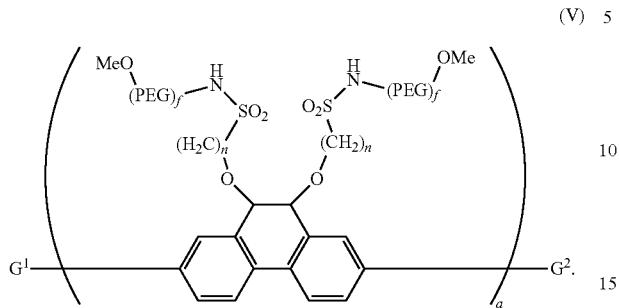

(V)

In some cases, the polymer is a copolymer and has the structure of Formula VI:

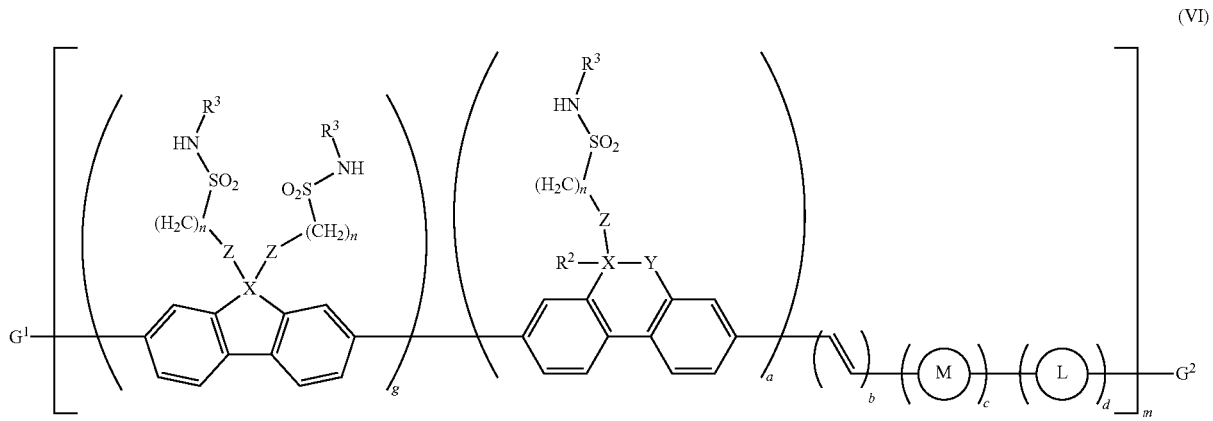

(VI)

wherein g and a together is a mol % from 10 to 100%.

In some cases, the polymer is a copolymer and has the structure of Formula VII:

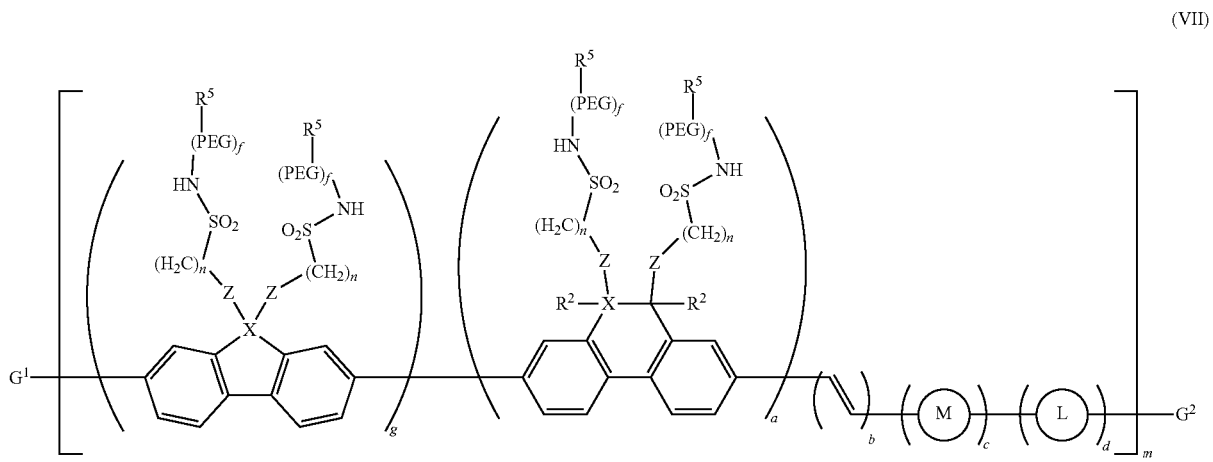

(VII)

wherein, each g and a together is a mol % from 10 to 100%; and each f is independently an integer from 0 to 50 and each $R^5$ is independently selected from the group consisting of H, $C_1$-$C_{12}$ alkyl, $C_2$-$C_{12}$ alkene, $C_2$-$C_{12}$ alkyne, $C_3$-$C_{12}$ cycloalkyl, $C_1$-$C_{12}$ haloalkyl, $C_1$-$C_{12}$ alkoxy, $C_2$-$C_{18}$ (hetero)aryloxy, $C_2$-$C_{18}$ (hetero)arylamino, and $C_1$-$C_{12}$ alkoxy.

In some cases, the polymer is a copolymer has the structure of Formula VIII:
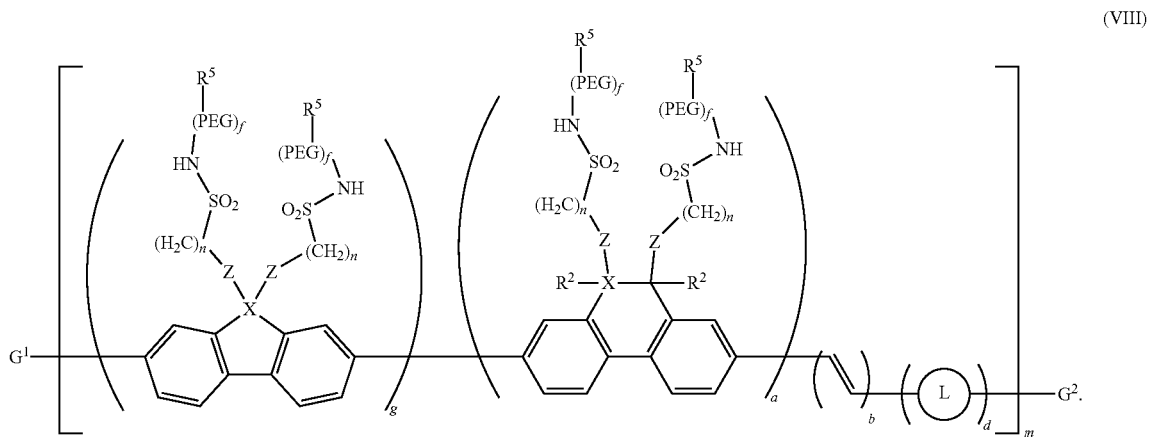
(VIII)
In some cases, the polymer is a copolymer and has the structure of Formula IX:
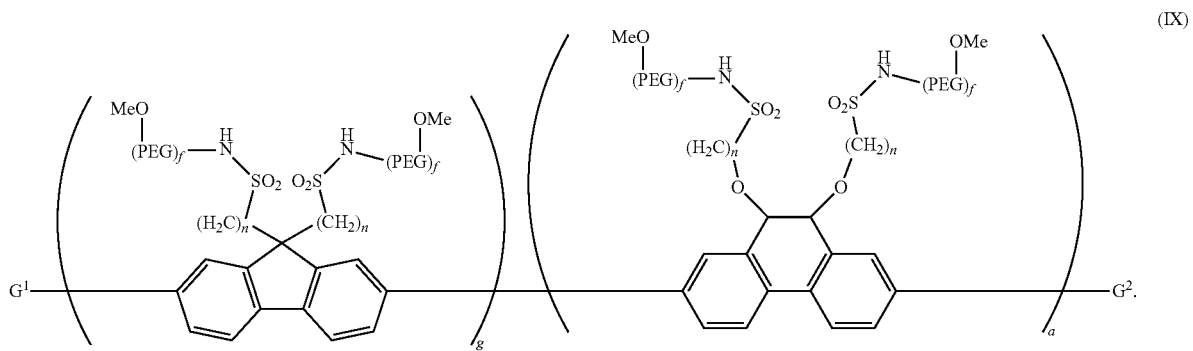
(IX)
In some embodiments, L is each independently selected from the group consisting of
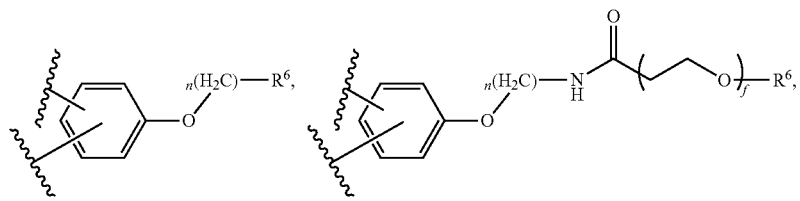
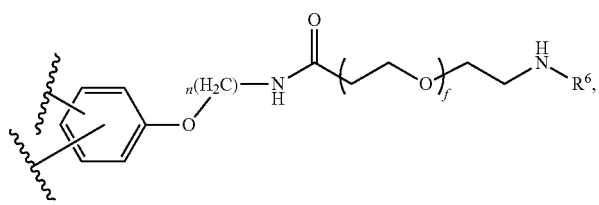

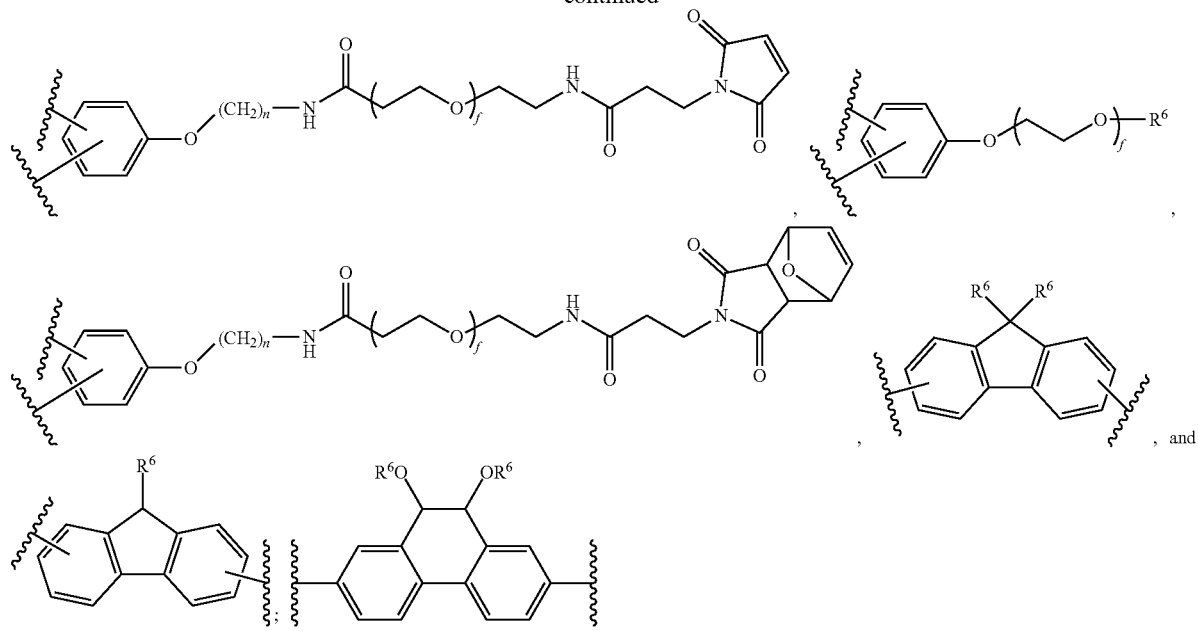

wherein, each $R^6$ is independently selected from the group consisting of H, OH, SH, NHCOO-t-butyl, $(CH_2)_n COOH$, $(CH_2)_n COOCH_3$, $(CH_2)_n NH_2$, $(CH_2)_n NH—(CH_2)_n—CH_3$, $(CH_2)_n NHCOOH$, $(CH_2)_n NHCO—(CH_2)_n—CO—(CH_2)_n—CH_3$, $(CH_2)_n NHCOO—(CH_2)_n—CH_3$, $(CH_2)_n NHCOOC(CH_3)_3$, $(CH_2)_n NHCO(C_3-C_{12})$cycloalkyl, $(CH_2)_n NHCO(CH_2CH_2O)_f$, $(CH_2)_n NHCO(CH_2)_n COOH$, $(CH_2)_n NHCO(CH_2)_n COO(CH_2)_n CH_3$, $(CH_2)_n (OCH_2CH_2)_f OCH_3$, N-maleimide, halogen, $C_2-C_{12}$ alkene, $C_2-C_{12}$ alkyne, $C_3-C_{12}$ cycloalkyl, $C_1-C_{12}$ halo alkyl, $C_1-C_{12}$ (hetero)aryl, $C_1-C_{12}$ (hetero)arylamino, and benzyl optionally substituted with one or more halogen, hydroxyl, $C_1-C_{12}$ alkoxy, or $(OCH_2CH_2)_f OCH_3$; each f is independently an integer from 0 to 50; and each n is independently an integer from 1 to 20.

In some embodiments, $G^1$ and $G^2$ are each independently selected from the group consisting of optionally substituted dihydrophenanthrene (DHP), optionally substituted fluorene, aryl substituted with one or more pendant chains terminated with a functional group, and a hetroaryl substituted with one or more pendant chains terminated with a functional group.

In some embodiments, $G^1$ and $G^2$ are each independently selected from the group consisting of

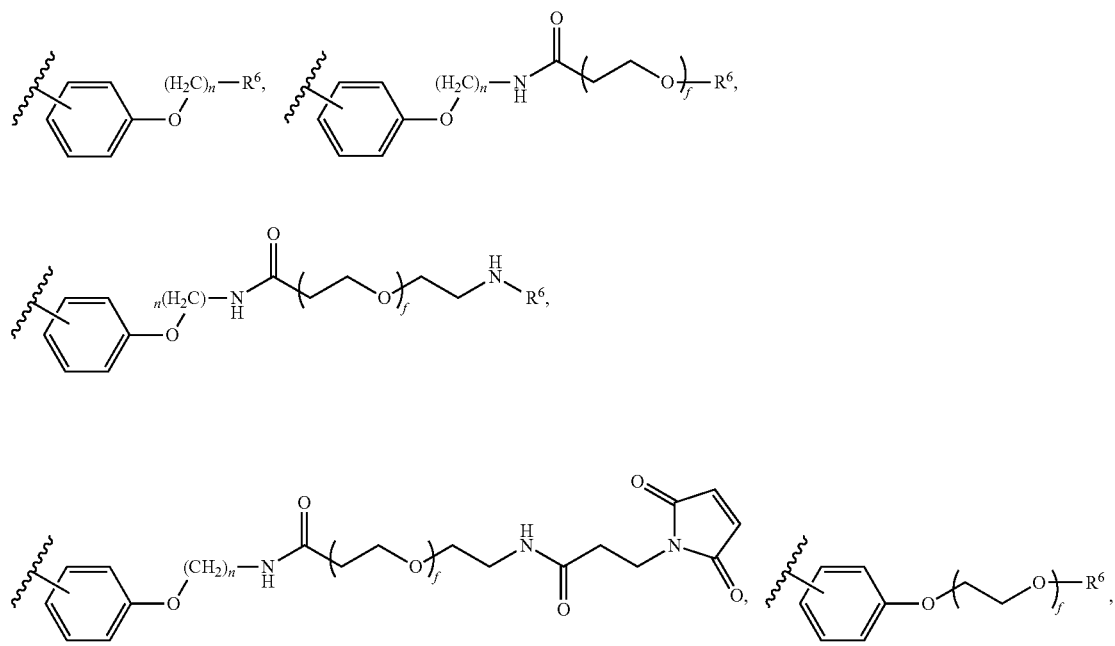

-continued

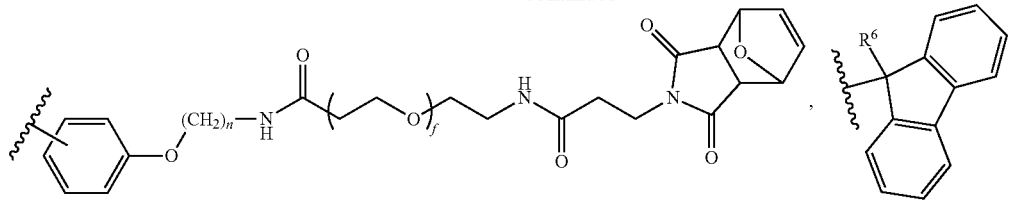

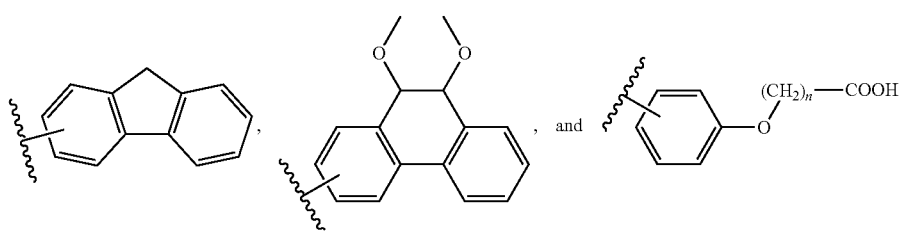, and 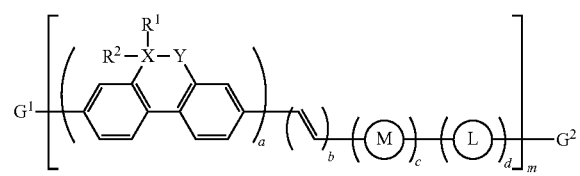

wherein, each $R^6$ is independently selected from the group consisting of H, OH, SH, NHCOO-t-butyl, $(CH_2)_n COOH$, $(CH_2)_n COOCH_3$, $(CH_2)_n NH_2$, $(CH_2)_n NH—(CH_2)_n—CH_3$, $(CH_2)_n NHCOOH$, $(CH_2)_n NHCO—(CH_2)_n—CO—(CH_2)_n—CH_3$, $(CH_2)_n NHCOO—(CH_2)_n—CH_3$, $(CH_2)_n NHCOOC(CH_3)_3$, $(CH_2)_n NHCO(C_3-C_{12})cycloalkyl$, $(CH_2)_n NHCO(CH_2CH_2O)_f$, $(CH_2)_n NHCO(CH_2)_n COOH$, $(CH_2)_n NHCO(CH_2)_n COO(CH_2)_n CH_3$, $(CH_2)_n(OCH_2CH_2)_f OCH_3$, N-maleimide, halogen, $C_2-C_{12}$ alkene, $C_2-C_{12}$ alkyne, $C_3-C_{12}$ cycloalkyl, $C_1-C_{12}$ halo alkyl, $C_1-C_{12}$ (hetero)aryl, $C_1-C_{12}$ (hetero)arylamino, and benzyl optionally substituted with one or more halogen, hydroxyl, $C_1-C_{12}$ alkoxy, or $(OCH_2CH_2)_f OCH_3$;

each f is independently an integer from 0 to 50; and
each n is independently an integer from 1 to 20.

In some embodiments, the present invention provides a method for detecting an analyte in a sample comprising:

providing a sample that is suspected of containing the analyte;

contacting the sample with a binding agent conjugated to a water soluble polymer having the structure of Formula I:

(I)

![Formula I structure]

wherein;

each X is independently selected from the group consisting of a C and Si;

each Y is independently selected from the group consisting of a bond, $CR^1R^2$, and $SiR^1R^2$;

when Y is a bond X is directly bonded to both rings;

each $R^1$ is independently selected from the group consisting of ammonium alkyl salt, ammonium alkyloxy salt, ammonium oligoether salt, sulfonate alkyl salt, sulfonate alkoxy salt, sulfonate oligoether salt, sulfonamido oligoether, and

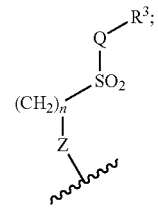

each $R^2$ is independently selected from the group consisting of H, alkyl, alkene, alkyne, cycloalkyl, haloalkyl, alkoxy, (hetero)aryloxy, aryl, (hetero)arylamino, PEG, ammonium alkyl salt, ammonium alkyloxy salt, ammonium oligoether salt, sulfonate alkyl salt, sulfonate alkoxy salt, sulfonate oligoether salt, sulfonamido oligoether, and

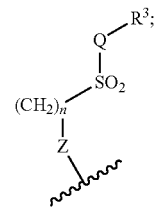

each $R^3$ is independently selected from the group consisting of H, alkyl, alkene, alkyne, cycloalkyl, haloalkyl, alkoxy, (hetero)aryloxy, aryl, (hetero)arylamino, and PEG;

each Z is independently selected from the group consisting of C, O, and N;

each Q is independently selected from the group consisting of a bond, NH, $NR^4$, and $CH_2$;

each M is independently an electron rich linker unit capable of altering the polymer band gap and is evenly or randomly distributed along the polymer main chain and is each independently selected from the group consisting of

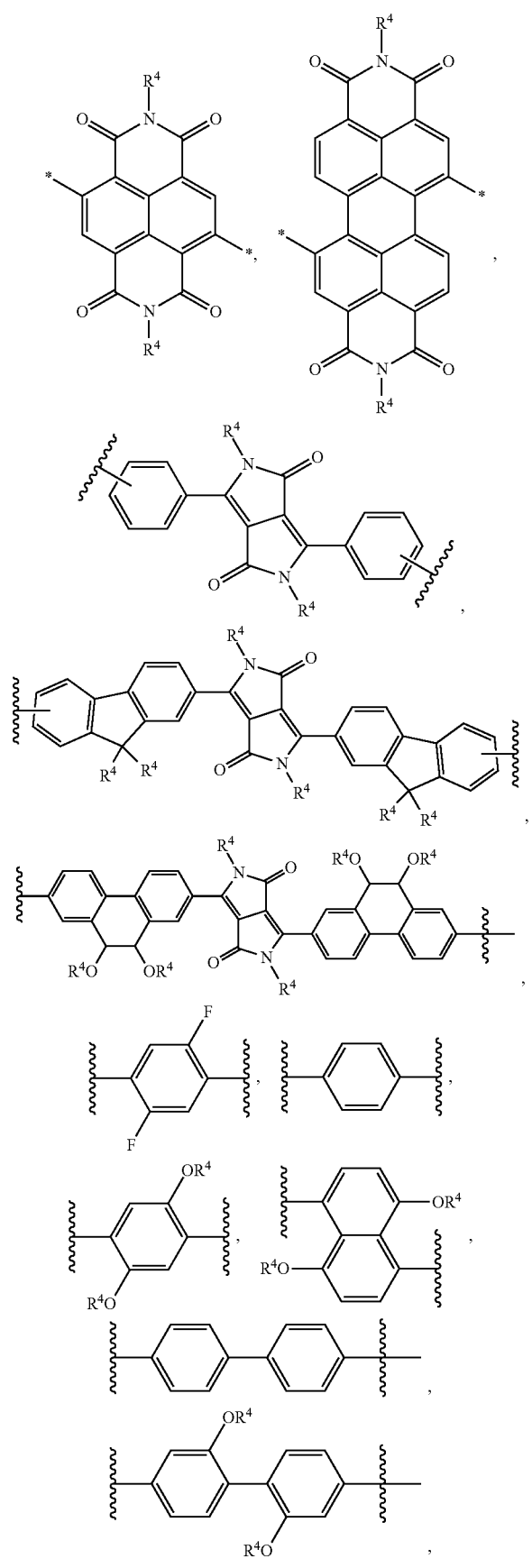

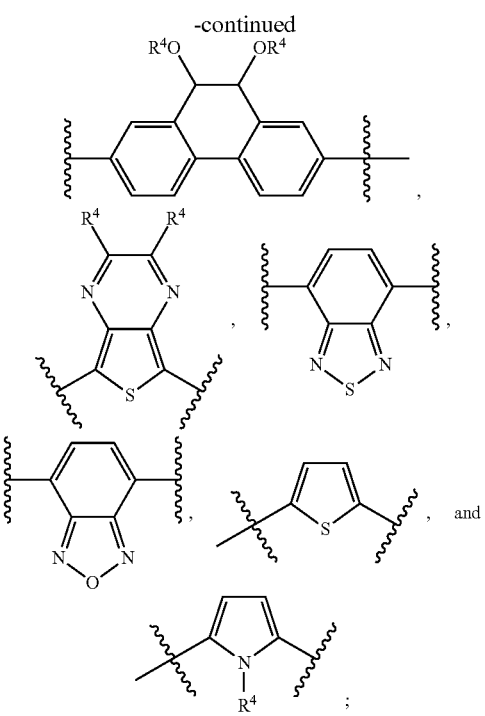

wherein, each $R^4$ is a non-ionic side group capable of imparting solubility in water in excess if 10 mg/mL and is each independently selected from the group consisting of halogen, hydroxyl, $C_1$-$C_{12}$ alkyl, $C_2$-$C_{12}$ alkene, $C_2$-$C_{12}$ alkyne, $C_3$-$C_{12}$ cycloalkyl, $C_1$-$C_{12}$ haloalkyl, $C_1$-$C_{12}$ alkoxy, $C_2$-$C_{18}$ (hetero)aryloxy, $C_2$-$C_{18}$ (hetero)arylamino, $(CH_2)_{x'}(OCH_2-CH_2)_{y'}OCH_3$ where each x' is independently an integer from 0-20; each y' is independently an integer from 0-50, and a $C_2$-$C_{18}$ (hetero) aryl group;

each optional linker L is an aryl or hetroaryl group evenly or randomly distributed along the polymer main chain and are substituted with one or more pendant chains terminated with a functional group selected from the group consisting of amine, carbamate, carboxylic acid, carboxylate, maleimide, activated ester, N-hydroxysuccinimidyl, hydrazine, hydrazide, hydrazone, azide, alkyne, aldehyde, thiol, and protected groups thereof for conjugation to another substrate, acceptor dye, molecule or binding agent;

$G^1$ and $G^2$ are each independently selected from the group consisting of hydrogen, halogen, alkyne, optionally substituted aryl, optionally substituted heteroaryl, halogen substituted aryl, silyl, diazonium salt, triflate, acetyloxy, azide, sulfonate, phosphate, boronic acid substituted aryl, boronic ester substituted aryl, boronic ester, boronic acid, optionally substituted dihydrophenanthrene (DHP), optionally substituted fluorene, aryl or hetroaryl substituted with one or more pendant chains terminated with a functional group selected from amine, carbamate, carboxylic acid, carboxylate, maleimide, activated ester, N-hydroxysuccinimidyl, hydrazine, hydrazide, hydrazone, azide, alkyne, aldehyde, thiol, and protected groups thereof for conjugation to a substrate or a binding agent;

a, c, and d define the mol % of each unit within the structure which each can be evenly or randomly repeated and where a is a mol % from 10 to 100%, c is a mol % from 0 to 90%, and each d is a mol % from 0 to 25%;
each b is independently 0 or 1;
m is an integer from 1 to about 10,000; and
each n is independently an integer from 1 to 20; and
wherein the binding agent is capable of interacting with the analyte or a target-associated biomolecule.

In some embodiments, the method further comprises, applying a light source to the sample that can excite the polymer; and detecting whether light is emitted from the conjugated polymer complex.

In some embodiments, the binding agent is a protein, peptide, affinity ligand, antibody, antibody fragment, sugar, lipid, nucleic acid or an aptamer. In some embodiments, the binding agent is an antibody.

In some embodiments, the method is configured for flow cytometry. In some embodiments, the binding agent is bound to a substrate. In some embodiments, the analyte is a protein expressed on a cell surface.

In some embodiments, the method is configured as a immunoassay. In some embodiments, the method further comprises providing additional binding agents for detecting additional analytes simultaneously.

BRIEF DESCRIPTION OF THE DRAWINGS

FIG. 4 shows the polymers of the present invention possess certain physical and chemical characteristics of absorption, fluorescence, brightness, molecular weight, polydispersity, dye to protein ratio when conjugated to an antibody etc. The preferred range of these parameters are shown in this table.

DETAILED DESCRIPTION OF THE INVENTION

I. General

Figure 1:
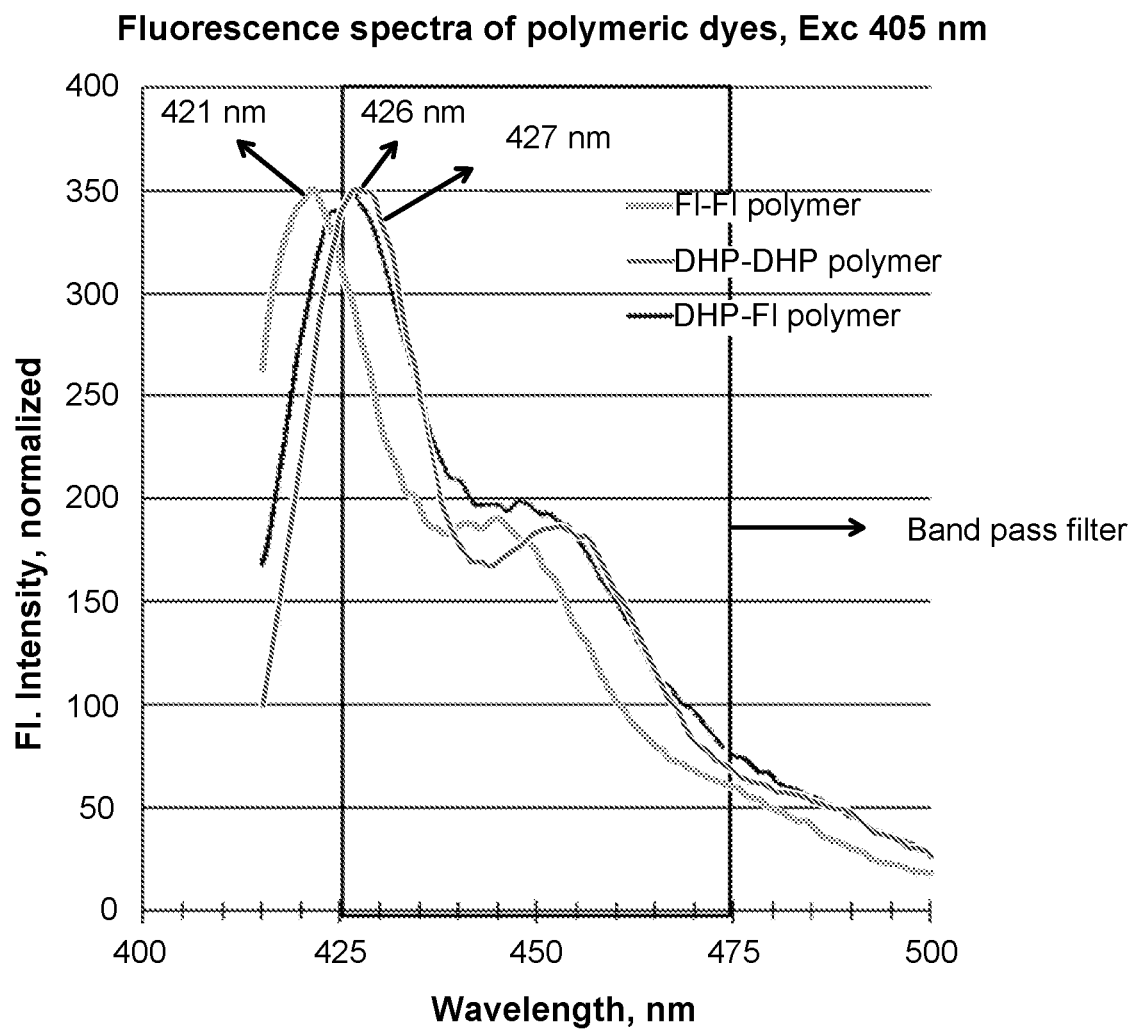
FIG. 1 shows a comparison of fluorescence emission spectra of fluorene (FF), dihydrophenanthrene (DD) and fluorene-DHP (DF) polymers.

The present invention provides novel, water soluble fluorescent polymers and methods for detecting analytes in a sample using complexes comprising the fluorescent polymers conjugated to binding agents. The water soluble conjugated polymers of present invention demonstrate significantly increased brightness compared to other dyes.

II. Definitions

The abbreviations used herein have their conventional meaning within the chemical and biological arts.

As used herein, the term "ammonium" refers to a cation having the formula $NHR_3^+$ where each R group, independently, is hydrogen or a substituted or unsubstituted alkyl, aryl, aralkyl, or alkoxy group. Preferably, each of the R groups is hydrogen.

As used herein, "oligoether" is understood to mean an oligomer containing structural repeat units having an ether functionality. As used herein, an "oligomer" is understood to mean a molecule that contains one or more identifiable structural repeat units of the same or different formula.

The term "sulfonate functional group" or "sulfonate," as used herein, refers to both the free sulfonate anion (—S(=O)$_2$O—) and salts thereof. Therefore, the term sulfonate encompasses sulfonate salts such as sodium, lithium, potassium and ammonium sulfonate.

The term "sulfonamido" as used herein refers to a group of formula —SO$_2$NR— where R is hydrogen, alkyl or aryl.

The term "alkyl" as used herein refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "cycloalkyl" as used herein refers to a saturated or partially unsaturated, monocyclic, fused bicyclic or bridged polycyclic ring assembly containing from 3 to 12 ring atoms, or the number of atoms indicated monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cyclooctyl, and norbornane.

The term "haloalkyl" as used herein refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, flouromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

As used herein, the term "halogen" refers to fluorine, chlorine, bromine and iodine.

The term "alkoxy" as used herein refers to an alkyl group, as defined above, having an oxygen atom that connects the alkyl group to the point of attachment. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

The term "alkene" as used herein refers to either a straight chain or branched hydrocarbon, having at least one double bond. Examples of alkene groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. The alkene group is typically monovalent, but can be divalent, such as when the alkenyl group links two moieties together.

The term "alkyne" as used herein refers to either a straight chain or branched hydrocarbon, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. The alkynyl group is typically monovalent, but can be divalent, such as when the alkynyl group links two moieties together.

The term "aryl" as used herein refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

The term "aryloxy" as used herein refers to a O-aryl group, wherein aryl is as defined above. An aryloxy group can be unsubstituted or substituted with one or two suitable substituents. The term "phenoxy" refers to an aryloxy group wherein the aryl moiety is a phenyl ring. The term "heteroaryloxy" as used herein means an —O-heteroaryl group, wherein heteroaryl is as defined below. The term "(hetero)aryloxy" is use to indicate the moiety is either an aryloxy or heteroaryloxy group.

The terms "Polyethylene glycol" or "PEG" as used herein refer to the family of biocompatible water-solubilizing linear polymers based on the ethylene glycol monomer unit.

The term "heteroaryl" as used herein refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, ($C_1$-$C_5$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

The term "(hetero)arylamino" as used herein refers an amine radical substituted with an aryl group (e.g., —NH-aryl). An arylamino may also be an aryl radical substituted with an amine group (e.g., -aryl-NH$_2$). Arylaminos may be substituted or unsubstituted.

The term "amine" as used herein refers to an alkyl groups as defined within, having one or more amino groups. The amino groups can be primary, secondary or tertiary. The alkyl amine can be further substituted with a hydroxy group. Amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

The term "carbamate" as used herein refers to the functional group having the structure —NR"CO$_2$R', where R' and R" are independently selected from hydrogen, ($C_1$-$C_8$) alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. Examples of carbamates include t-Boc, Fmoc, benzyloxy-carbonyl, alloc, methyl carbamate, ethyl carbamate, 9-(2-sulfo)fluorenylmethyl carbamate, 9-(2,7-dibromo)fluorenylmethyl carbamate, Tbfmoc, Climoc, Bimoc, DBD-Tmoc, Bsmoc, Troc, Teoc, 2-phenylethyl carbamate, Adpoc, 2-chloroethyl carbamate, 1,1-dimethyl-2-haloethyl carbamate, DB-t-BOC, TCBOC, Bpoc, t-Bumeoc, Pyoc, Bnpeoc, V-(2-pivaloylamino)-1,1-dimethylethyl carbamate, NpSSPeoc.

The term "carboxylate" as used herein refers to the conjugate base of a carboxylic acid, which generally can be represented by the formula RCOO. For example, the term "magnesium carboxylate" refers to the magnesium salt of the carboxylic acid.

The term "activated ester" as used herein refers to carboxyl-activating groups employed in peptide chemistry to promote facile condensation of a carboxyl group with a free amino group of an amino acid derivative. Descriptions of these carboxyl-activating groups are found in general textbooks of peptide chemistry; for example K. D. Kopple, "Peptides and Amino Acids", W. A. Benjamin, Inc., New York, 1966, pp. 50-51 and E. Schroder and K. Lubke, "The Peptides"; Vol. 1, Academic Press, New York, 1965, pp. 77-128.

The terms "hydrazine" and "hydrazide" refer to compounds that contain singly bonded nitrogens, one of which is a primary amine functional group.

The term "aldehyde" as used herein refers to a chemical compound that has an —CHO group.

The term "thiol" as used herein refers to a compound that contains the functional group composed of a sulfur-hydrogen bond. The general chemical structure of the thiol functional group is R—SH, where R represents an alkyl, alkene, aryl, or other carbon-containing group of atoms.

The term "silyl" as used herein refers to $Si(R^z)_3$ wherein each $R^z$ independently is alkyl aryl or other carbon-containing group of atoms.

The term "diazonium salt" as used herein refers to a group of organic compounds with a structure of $R-N_2^+X^-$, wherein R can be any organic residue (e.g., alkyl or aryl) and X is an inorganic or organic anion (e.g., halogen).

The term "triflate" also referred to as trifluoromethanesulfonate, is a group with the formula $CF_3SO_3$.

The term "boronic acid" as used herein refers to a structure —$B(OH)_2$. It is recognized by those skilled in the art that a boronic acid may be present as a boronate ester at various stages in the synthesis of the quenchers. Boronic acid is meant to include such esters. The term "boronic ester" or "boronate ester" as used herein refers to a chemical compound containing a —$B(Z^1)(Z^2)$ moiety, wherein $Z^1$ and $Z^2$ together form a moiety where the atom attached to boron in each case is an oxygen atom. In some embodiments, the boronic ester moiety is a 5-membered ring. In some other embodiments, the boronic ester moiety is a 6-membered ring. In some other embodiments, the boronic ester moiety is a mixture of a 5-membered ring and a 6-membered ring.

III. Compositions

Polymers

The compounds of the present invention comprise water soluble fluorescent polymers having the structure of Formulas I-XIII. In some embodiments, polymers of the present invention utilize dihydrophenanthrene (DHP), fluorene, and combinations of DHP and fluorene monomers as shown in Formula I:

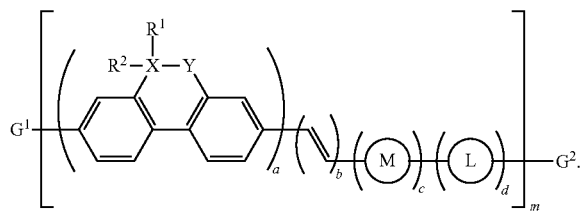

The polymers complexes of the present invention can contain units capable of altering the polymer band gap and are evenly or randomly distributed along the polymer main chain. These unites are represented in Formula I as M. The polymers complexes of the present invention can also contain linkers represented in Formula I as L. Each optional linker L is an aryl or hetroaryl group evenly or randomly distributed along the polymer main chain and are substituted with one or more pendant chains terminated with a functional group selected from the group consisting of amine, carbamate, carboxylic acid, carboxylate, maleimide, activated ester, N-hydroxysuccinimidyl, hydrazine, hydrazide, hydrazone, azide, alkyne, aldehyde, thiol, and protected groups thereof for conjugation to a substrate or binding agent.

The polymers complexes of the present invention also contain capping units represented in Formula I as each $G^1$ and $G^2$, which are each independently selected from the group consisting of hydrogen, halogen, alkyne, optionally substituted aryl, optionally substituted heteroaryl, halogen substituted aryl, silyl, diazonium salt, triflate, acetyloxy, azide, sulfonate, phosphate, boronic acid substituted aryl, boronic ester substituted aryl, boronic ester, boronic acid, optionally substituted dihydrophenanthrene (DHP), optionally substituted fluorene, aryl or hetroaryl substituted with one or more pendant chains terminated with a functional group selected from amine, carbamate, carboxylic acid, carboxylate, maleimide, activated ester, N-hydroxysuccinimidyl, hydrazine, hydrazide, hydrazone, azide, alkyne, aldehyde, thiol, and protected groups thereof for conjugation to a substrate or binding agent.

In some cases, the polymer has the structure of Formula II:

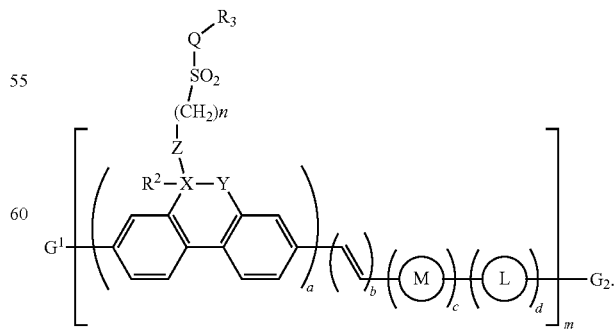

In some cases the polymer has the structure of Formula IV:
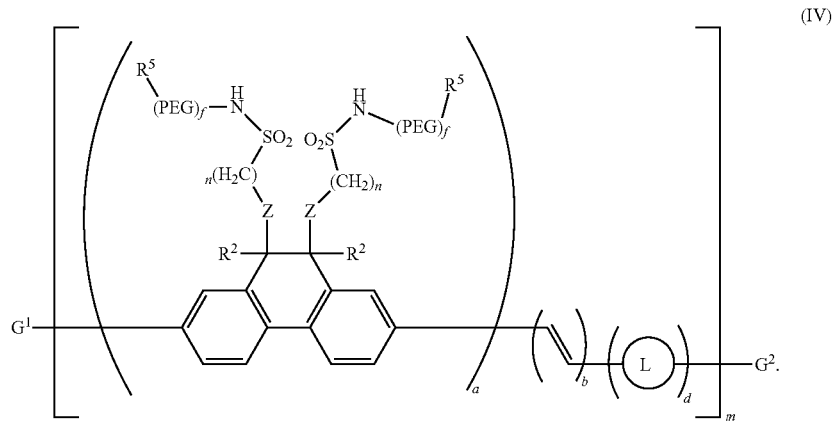
(IV)
In some cases, the polymer has the structure of Formula V:
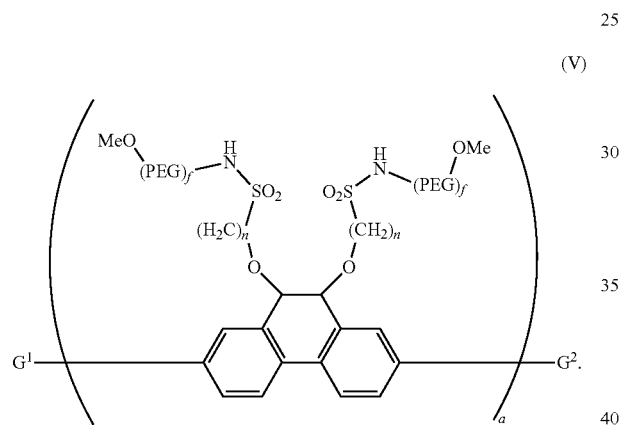
(V)
In some cases, the polymer is a copolymer and has the structure of Formula VI:
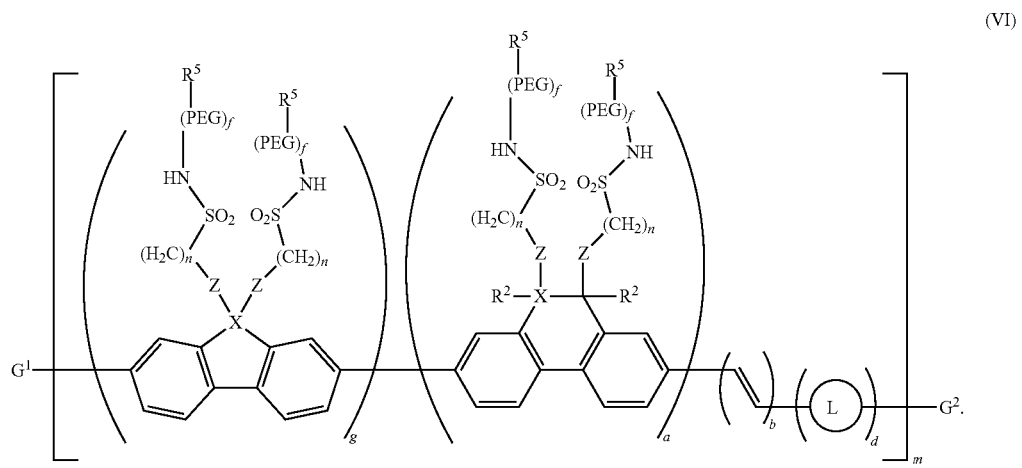
(VI)

In some cases, the polymer is a copolymer and has the structure of Formula VII:

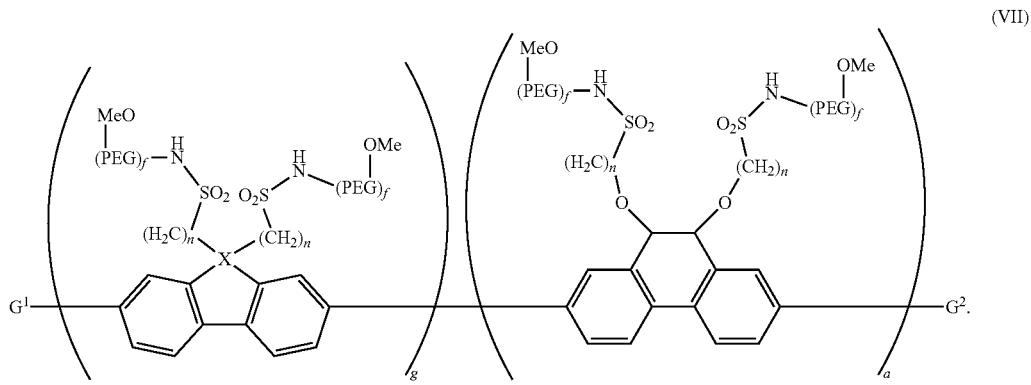

(VII)

In some embodiments, the polymer has acceptor dyes attached to the backbone that will allow to excite the polymer backbone and see monitor the emission of the acceptor dyes attached to the back bone through energy transfer. Acceptor dyes useful in the invention include FITC, CY3B, Cy55, Alexa 488, Texas red, Cy5, Cy7, Alexa 750, and 800CW. For example, polymers with acceptor dyes of the present invention include:

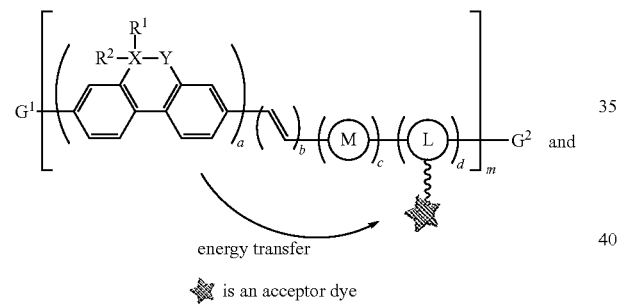

energy transfer is an acceptor dye

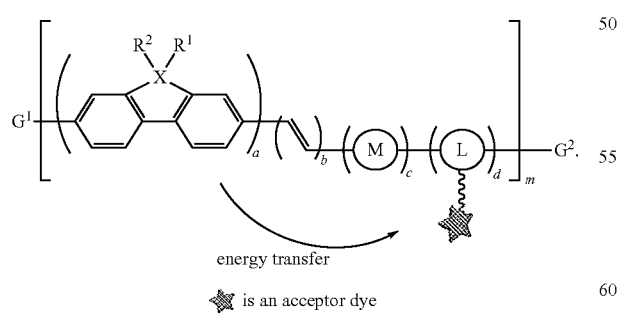

energy transfer is an acceptor dye

Monomers

Monomers of the present invention include dihydrophenanthrene (DHP) and fluorene based monomers. For example, monomers of the present invention include:

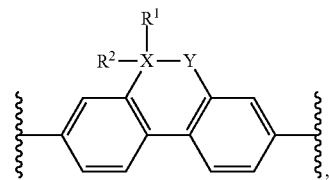

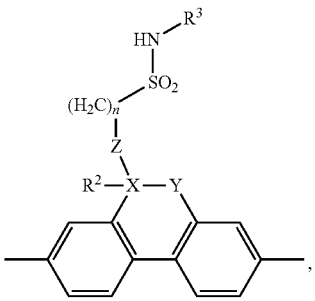

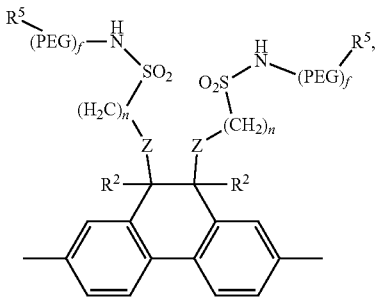

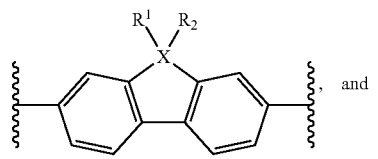

and

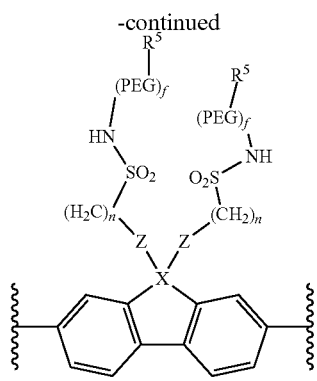

Where both terminal ends of the monomers are independently or both a halogen atom, boronic ester or boronic acid, silyl, diazonium salt, triflate, acetyloxy, sulfonate, or phosphate which can undergo Pd or Nickel salt catalyzed polymerization reactions. $R^1$ is independently a side group capable of imparting solubility in water/buffer and each $R^1$ is independently selected from the group consisting of ammonium alkyl salt, ammonium alkyloxy salt, ammonium oligoether salt, sulfonate alkyl salt, sulfonate alkoxy salt, sulfonate oligoether salt, sulfonamido oligoether, and

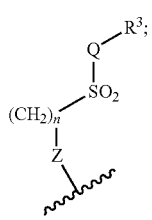

each $R^2$ is independently selected from the group consisting of H, alkyl, alkene, alkyne, cycloalkyl, haloalkyl, alkoxy, (hetero)aryloxy, aryl, (hetero)arylamino, PEG, ammonium alkyl salt, ammonium alkyloxy salt, ammonium oligoether salt, sulfonate alkyl salt, sulfonate alkoxy salt, sulfonate oligoether salt, sulfonamido oligoether, and

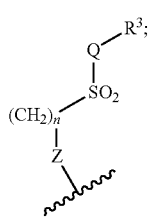

each $R^3$ is independently selected from the group consisting of H, alkyl, alkene, alkyne, cycloalkyl, haloalkyl, alkoxy, (hetero)aryloxy, aryl, (hetero)arylamino, and PEG; each Z is independently selected from the group consisting of C, O, and N; each Q is independently selected from the group consisting of a bond, NH, $NR^4$ and $CH_2$; and each $R^5$ is independently selected from the group consisting of H, $C_1$-$C_{12}$ alkyl, $C_2$-$C_{12}$ alkene, $C_2$-$C_{12}$ alkyne, $C_3$-$C_{12}$ cycloalkyl, $C_1$-$C_{12}$ haloalkyl, $C_1$-$C_{12}$ alkoxy, $C_2$-$C_{18}$ (hetero)aryloxy, $C_2$-$C_{18}$ (hetero)arylamino, and $C_1$-$C_{12}$ alkoxy.

In some embodiments, monomers of the present invention also include bridged monomers. For example, bridged monomers of the present invention include:

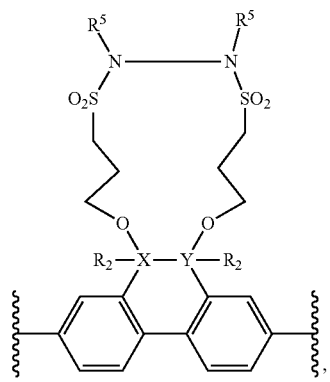

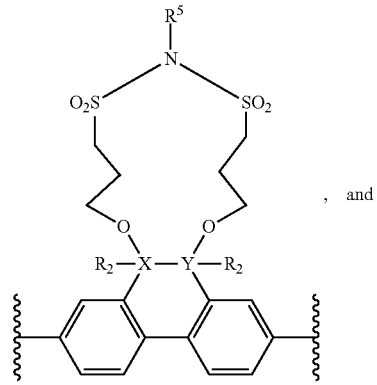

, and

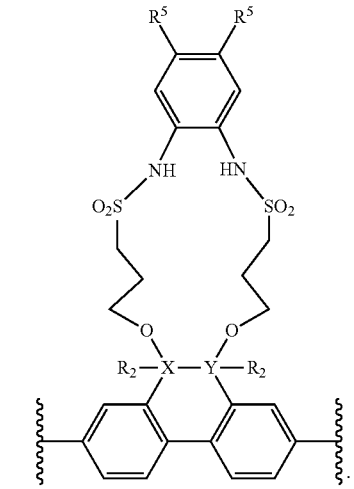

.

Synthesis

DHP monomers of the present invention can be made as shown below.

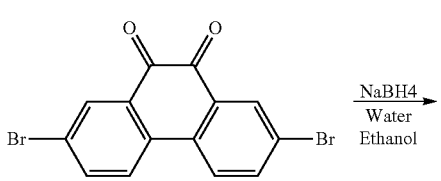

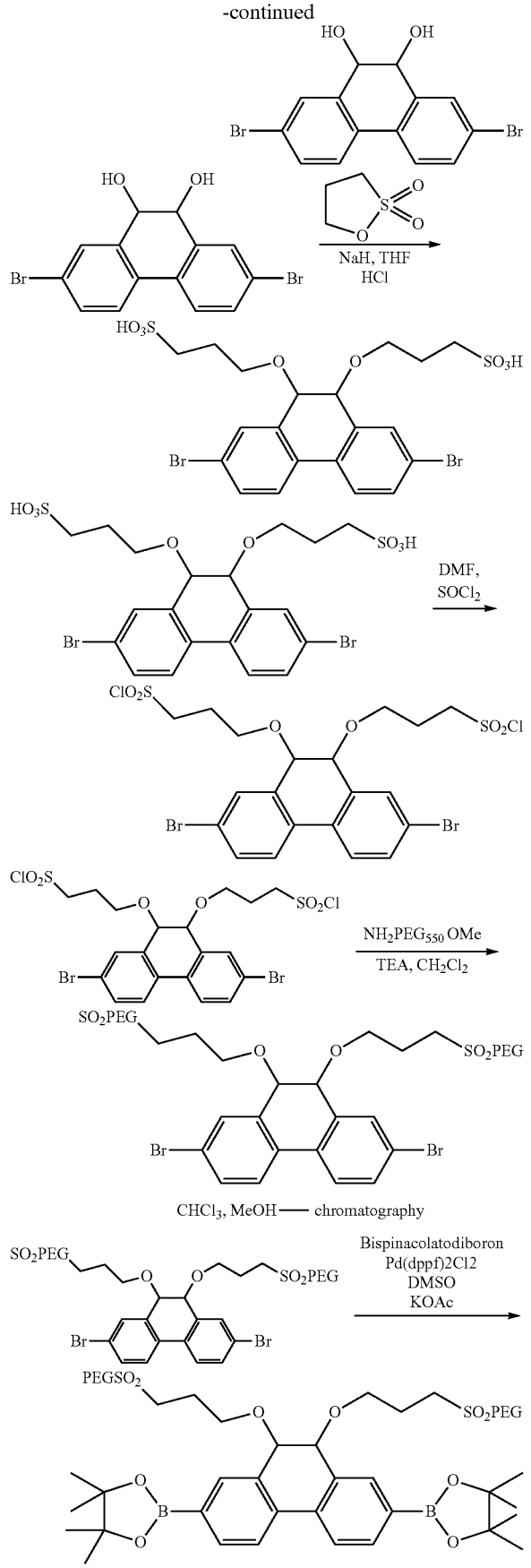

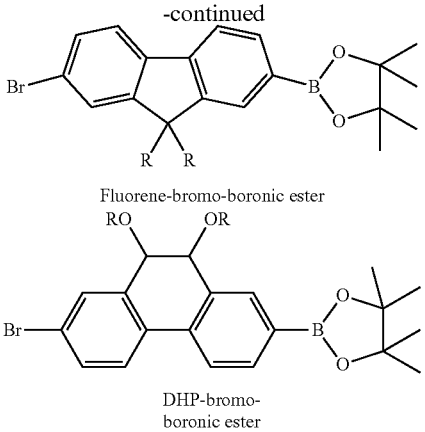

Fluorene-bromo-boronic ester

DHP-bromo-boronic ester

For example, 2,7-dibromo-trans-9,10-dihydrophenanthrene-9,10-diol (DHP—OH) can be prepared as follows. In a conical flask (2000 L), add about 26 g of NaBH₄ into a stirring water-ethanol mixture (120 mL+780 mL). To this solution, add about 24 g of 2,7-dibromophenanthrene,9, 10-dione portion-wise but quickly (in 5 min). The reaction mix allowed stirring for a day. The color of the solution changes from orange red to pale yellow to white by the end of the reaction. Stop the reaction and neutralize the reaction mixture with dil HCl acid. After the neutralization, filter the white precipitate and wash with excess water. Thus obtained white precipitate was washed with very cold (<−15° C.) ethanol (100 mL) and Methanol (100 mL).

DHP—OSO₃H can be prepared as follows. In a 2 neck round bottom flask, DHP—OH (3.6 g) and 18C6 (500 mg) were dissolved in 120 mL of THF. The solution was purged with nitrogen (20 min) and NaH (2 g) was added while nitrogen purging continues. The color of the solution changes from colorless to pale pink, dark pink, brown and dark green in 10-15 min. In another RB, 12 g of 1,3 propane sultone was dissolved in 20 mL of THF and nitrogen purged. This sultone solution was added to DHP—OH solution by addition funnel over a period of 20-30 minutes. The reaction was stirred at RT for 4-5 hrs. The solvents were evaporated, and dissolved the precipitate in water. Acetone was added to obtain white precipitate of DPS in the form of disodium salt. Filter the precipitate and redissolve in water (minimal amount) neutralize with HCl and precipitate again in acetone. Repeated precipitation (2-3 times) followed by centrifugation gives DPS as white solid.

DHP—OSO₂Cl can be prepared as follows. 5 g of DHP—OSO₃H was taken in a round bottom flask and mixed with 25 mL of DMF. To this about 10 mL of SOCl₂ was added dropwise and the mixture allowed to stir for overnight. Next morning, reaction mixture was poured into 200 mL water and precipitate was filtered and dried.

DHP-sulfonamide PEG can be prepared as follows. DHP—OSO₂Cl was mixed with 2.2 equivalent of PEG amine in dichloromethane/TEA mixture. After 3 h sonication reaction the crude product was extracted in dichloromethane followed by column chromatography (silica gel, MeOH—CHCl₃).

Diboronic ester of DHP-sulfonamide PEG can be prepared as follows. The dibromo compound was mixed with DMSO under nitrogen and to this 3 equivalent of bispinacolatodiboron was added. The reagents were reacted with 12 equivalent of potassium acetate and 4 equivalent of Pd(dppf)Cl₂ catalyst for 5 hours at 80deg. Reaction mixture cooled down and extracted with CHCl3/water. The organic layer was concentrated and purified by column chromatography (silica gel, MeOH—CHCl$_3$).

Similarly, Fluorene monomers of the present invention can be made as described below. For example, FL-OSO$_3$H can be prepared as follows. In a 2 neck round bottom flask, 5 g of Fluorene was mixed with in 70 of DMSO. The solution was purged with nitrogen (20 min) and 50% NaOH (12 eq) was added while nitrogen purging continues. The color of the solution changes from colorless to dark brown. Propane sultone (3 eq) was weighed and dissolved in DMSO. This was added to the fluorene reaction mixture dropwise over a period of 5 minutes. The reaction was stirred at RT for 4-5 hrs. The solvents were evaporated, and dissolved the precipitate in water. Acetone was added to obtain white precipitate of DPS in the form of disodium salt. Filter the precipitate and redissolve in water (minimal amount) neutralize with HCl and precipitate again in acetone. Repeated precipitation (2-3 times) followed by centrifugation gives FL-OSO$_3$H as white solid.

FL-OSO$_2$Cl can be prepared as follows. 5 g of FL-OSO$_3$H was taken in a round bottom flask and mixed with 25 mL of DMF. To this about 10 mL of SOCl$_2$ was added dropwise and the mixture allowed to stir for overnight. Next morning, reaction mixture was poured into 200 mL water and precipitate was filtered and dried.

FL-sulfonamide PEG can be prepared as follows. FL-OSO$_2$Cl was mixed with 2.2 equivalent of PEG amine in dichloromethane/TEA mixture. After 3 h sonication reaction the crude product was extracted in dichloromethane followed by column chromatography (silica gel, MeOH—CHCl$_3$).

Diboronic ester of FL-sulfonamide PEG can be prepared as follows. The dibromo compound was mixed with DMSO under nitrogen and to this 3 equivalent of bispinacolatodiboron was added. The reagents were reacted with 12 equivalent of potassium acetate and 4 equivalent of Pd(dppf)Cl$_2$ catalyst for 5 hours at 80deg. Reaction mixture cooled down and extracted with CHCl$_3$/water. The organic layer was concentrated and purified by column chromatography (silica gel, MeOH—CHCl$_3$).

Polymerization

The compounds described in the above embodiments may be made using procedures known in the art. In some embodiments, fluorescent polymers can be made from dihydrophenanthrene (DHP) monomers combined with electron rich linker units. In some embodiments, bright polymeric dyes can be made from fluorene monomers combined with electron rich linker units. In some embodiments, bright polymeric dyes can be made from a combination of DHP and fluorene monomers combined with electron rich linker units.

Generally, polymerization monomer units described above can be accomplished using polymerization techniques known to those of skill in the art or using methods known in the art in combination with methods described herein. For example, Synthesis of diboronic ester derivatives from a dihalide monomer can be accomplished via Suzuki coupling with bis(pinacolato) diboron:

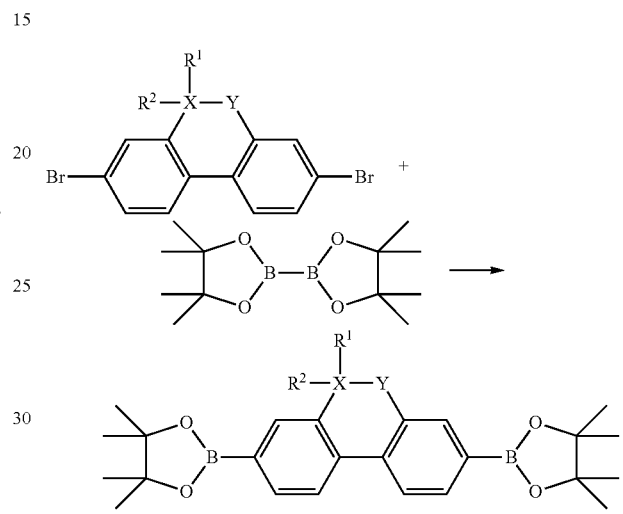

Similarly, polymerization can also be achieved via Suzuki coupling:

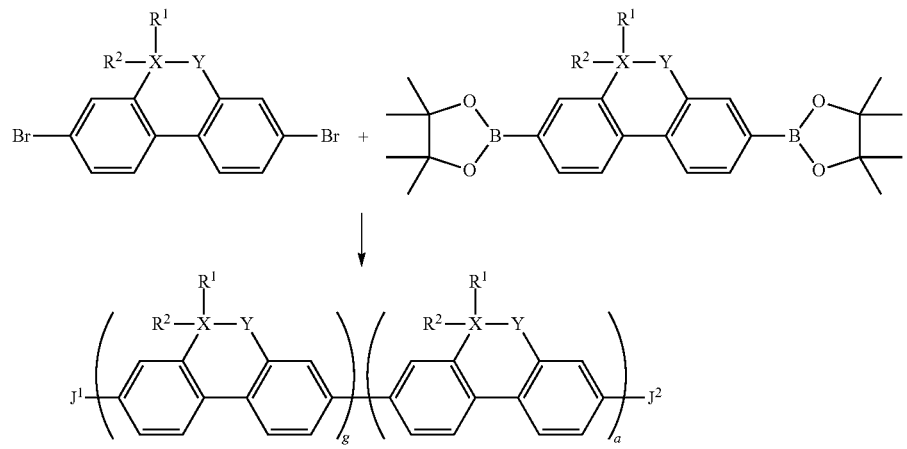

Where $J^1$ and $J^2$ are independently H, Br, B(OH)$_2$, or a boronic ester.

For example, polymerization can proceed as follows. In a round bottom flask both the bromo and boronic monomers were taken in (DMF-water) mixture and purged with nitrogen for 10 minutes. Under nitrogen about 20 equivalent of CsF and 10% of Pd(OAc)2 were mixed and heated at 800 Celcius. Polymerization was monitored using UV-Vis spectroscopy and SEC chromatography. Later to the reaction mixture, a capping agent (selected from G1) containing appropriate functional group was added and 3 hours later the second capping agent (selected from G2) added. After the reaction the crude reaction mixture was evaporated off and passed through a gel filtration column to remove small organic molecules and low MW oligomers.

Capping Units

Linkers and capping units can be conjugated to a polymer backbone of this invention via similar mechanisms as described previously. For example, bromo- and boronic esters of capping units can be used to append one or both ends of a polymer. Utilizing both bromo- and boronic esters of capping units will append both ends of polymer. Utilizing only one form, either a bromo- or boronic ester of a capping unit, will append only those ends terminated with its respective complement and for symmetric polymerizations can be used to statistically modify only one end of a polymer. For asymmetric polymers this approach is used to chemically ensure the polymers are only modified at a single chain terminus. Capping units can also be appended asymmetrically by first reacting a bromo-capping unit with a polymer with Y ends and subsequently reacting the polymer with a boronic ester capping unit.

For example, capping agents of the present invention can be made as shown below.

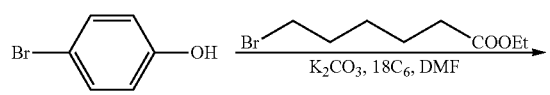

Binding Agents

A "binding agent" of the invention can be any molecule or complex of molecules capable of specifically binding to target analyte. A binding agent of the invention includes for example, proteins, small organic molecules, carbohydrates (including polysaccharides), oligonucleotides, polynucleotides, lipids, affinity ligand, antibody, antibody fragment, an aptamer and the like. In some embodiments, the binding agent is an antibody or fragment thereof. Specific binding in the context of the present invention refers to a binding reaction which is determinative of the presence of a target analyte in the presence of a heterogeneous population. Thus, under designated assay conditions, the specified binding agents bind preferentially to a particular protein or isoform of the particular protein and do not bind in a significant amount to other proteins or other isoforms present in the sample.

When the binding agents are antibodies, they may be monoclonal or polyclonal antibodies. The term antibody as used herein refers to immunoglobulin molecules and immunologically active portions of immunoglobulin (Ig) molecules. Such antibodies include, but are not limited to, polyclonal, monoclonal, mono-specific polyclonal antibodies, antibody mimics, chimeric, single chain, Fab, Fab' and F(ab')$_2$ fragments, Fv, and an Fab expression library.

Complexes

In general, fluorescent polymers of the present invention can be conjugated to binding agents using techniques known to those of skill in the art or using methods known in the art in combination with methods described herein.

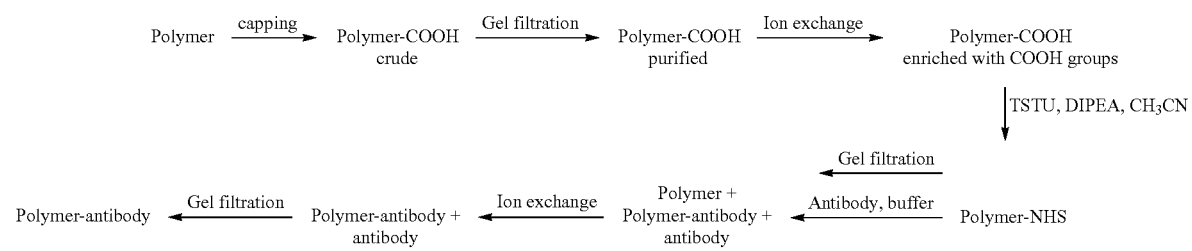

-continued

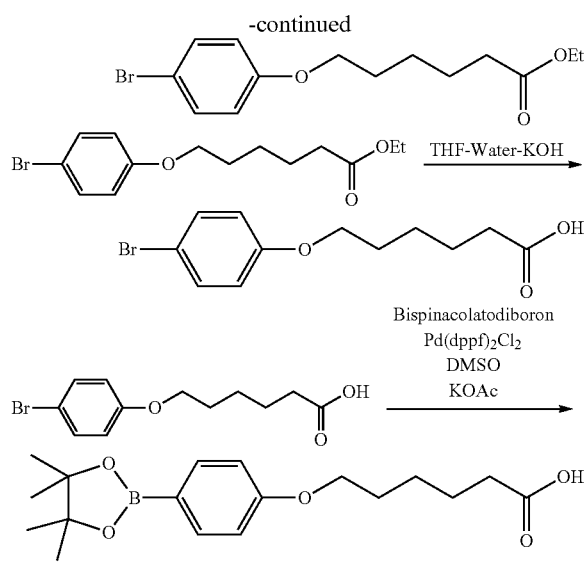

For example, preparation of polymer NHS ester can proceed as follows. Take 5 mg of the polymer in a clean vial and dissolve in 1 mL dry CH$_3$CN. To this add 15 mg TSTU and stir for 2 more minutes. To this add 100 uL DIPEA and continue stirring for overnight with the cap sealed with parafilm. Later evaporate off the organic solvents in the reaction mixture Dissolve the crude NHS in about 750 uL of 1×BBS buffer (pH 8.8) by a quick vortex and transfer it to the Zeba column 40K MWCO. Spin down the sample at 2200 RPM for 2 min and use this polymer NHS immediately.

Conjugation of polymer NHS with CD4 can proceed as follows. Take the polymer NHS in 1×BBS (~800 uL) which was spun down, add to 0.6 mg of CD4 and mix with 100 uL of 0.5M Borate buffer (pH 9.0). Vortex quickly for 30 seconds and allow to mix for 3-4 hours in the coulter mix.

Purification of conjugate through Histrap HP column can proceed as follows. Approach 1: After the crude reaction purify the conjugate using a Histrap HP column. Load the sample using 1×PBS buffer and collect the unbound fraction. This can be done using 20 CV of buffer. Later change the buffer to wash the bound fraction which has both conjugate and free antibody. This can be done using 1×PBS with 0.25M imidazole running for 10 CV.

Approach 2: Hitrap SP Sepharose FF column. Equilibrate the column and load the sample using 20 mM Citrate buffer pH 3.5 and collect the unbound fraction. This can be done using 20 CV of buffer. Later change the buffer to elute the bound fraction which has both conjugate and free antibody. This can be done using 20 mM Tris buffer pH 8.5 running for 20 CV.

Approach 3: Load the crude conjugate in a Tangential flow filtration system equipped with a 300K MWCO membrane. The conjugate is washed using 1×PBS until the filtrate show no absorption at 405 nm. Later the compound is concentrated.

Purification of conjugate through SEC column can proceed as follows. Load the crude conjugate containing free antibody to the Size Exclusion Column, using 1×PBS. Pool the tubes after checking the absorption spectra and concentrate in a Amicon Ultra-15 having a 30 KDa MWCO centrifugal concentrator.

IV. Methods of Detecting an Analyte

Overview

The present invention provides a method for detecting an analyte in a sample comprising: providing a sample that is suspected of containing an analyte; providing a conjugated polymer complex, which comprises a binding agent conjugated to a water soluble conjugated polymer. The binding agent is capable of interacting with the analyte. A light source is applied to the sample that can excite the polymer and light emitted from the conjugated polymer complex is detected. In the typical assay, fluorescent polymers of the invention are excitable with a light having wavelength between about 395 nm and about 415 nm. The emitted light is typically between about 415 nm and about 475 nm. Alternatively, excitation light can have a wavelength between about 340 nm and about 370 nm and the emitted light is between about 390 nm and about 420 nm.

Sample

The sample in the methods of the present invention can be, for example, blood, bone marrow, spleen cells, lymph cells, bone marrow aspirates (or any cells obtained from bone marrow), urine (lavage), serum, saliva, cerebral spinal fluid, urine, amniotic fluid, interstitial fluid, feces, mucus, or tissue (e.g., tumor samples, disaggregated tissue, disaggregated solid tumor). In certain embodiments, the sample is a blood sample. In some embodiments, the blood sample is whole blood. The whole blood can be obtained from the subject using standard clinical procedures. In some embodiments, the sample is a subset of one or more cells of whole blood (e.g., erythrocyte, leukocyte, lymphocyte (e.g., T cells, B cells or NK cells), phagocyte, monocyte, macrophage, granulocyte, basophil, neutrophil, eosinophil, platelet, or any cell with one or more detectable markers). In some embodiments, the sample can be from a cell culture.

The subject can be a human (e.g., a patient suffering from a disease), a commercially significant mammal, including, for example, a monkey, cow, or horse. Samples can also be obtained from household pets, including, for example, a dog or cat. In some embodiments, the subject is a laboratory animal used as an animal model of disease or for drug screening, for example, a mouse, a rat, a rabbit, or guinea pig.

Analytes

An "analyte" as used herein, refers to a substance, e.g., molecule, whose abundance/concentration is determined by some analytical procedure. For example, in the present invention, an analyte can be a protein, peptide, nucleic acid, lipid, carbohydrate or small molecule.

The target analyte may be, for example, nucleic acids (DNA, RNA, mRNA, tRNA, or rRNA), peptides, polypeptides, proteins, lipids, ions, monosaccharides, oligosaccharides, polysaccharides, lipoproteins, glycoproteins, glycolipids, or fragments thereof. In some embodiments, the target analyte is a protein and can be, for example, a structural microfilament, microtubule, and intermediate filament proteins, organelle-specific markers, proteasomes, transmembrane proteins, surface receptors, nuclear pore proteins, protein/peptide translocases, protein folding chaperones, signaling scaffolds, ion channels and the like. The protein can be an activatable protein or a protein differentially expressed or activated in diseased or aberrant cells, including but not limited to transcription factors, DNA and/or RNA-binding and modifying proteins, nuclear import and export receptors, regulators of apoptosis or survival and the like.

Assays

Assay systems utilizing a binding agent and a fluorescent label to quantify bound molecules are well known. Examples of such systems include flow cytometers, scanning cytometers, imaging cytometers, fluorescence microscopes, and confocal fluorescent microscopes.

In some embodiments, flow cytometry is used to detect fluorescence. A number of devices suitable for this use are available and known to those skilled in the art. Examples include BCI Navios, Gallios, Aquios, and CytoFLEX flow cytometers.

In other embodiments, the assay is an immunoassay. Examples of immunoassays useful in the invention include, but are not limited to, fluoroluminescence assay (FLA), and the like. The assays can also be carried out on protein arrays.

When the binding agents are antibodies, antibody or multiple antibody sandwich assays can also be used. A sandwich assay refers to the use of successive recognition events to build up layers of various binding agents and reporting elements to signal the presence of a particular analyte. Examples of sandwich assays are disclosed in U.S. Pat. No. 4,486,530 and in the references noted therein.

V. Examples

Example 1: Preparation of DHP Polymer Complex

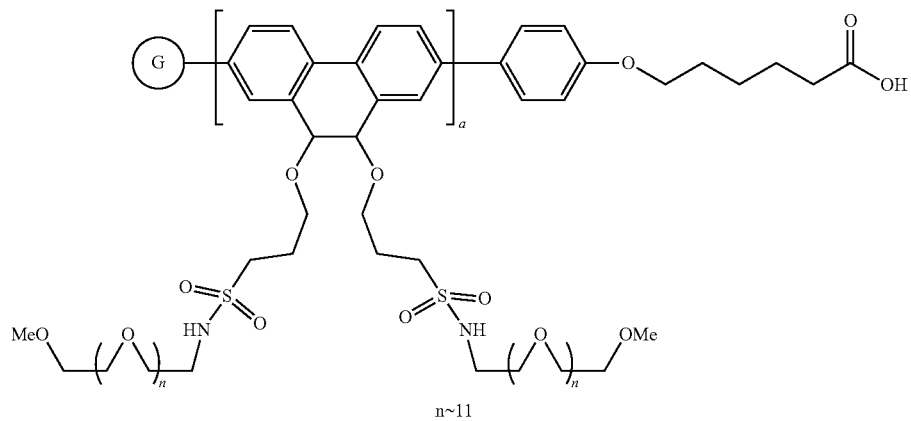

n~11

Method 1: In a round bottom flask both the dibromo DHP and diboronic DHP monomers (1:1) were taken in (DMF-water) mixture and purged with nitrogen for 10 minutes. Under nitrogen about 20 equivalent of CsF and 10% of Pd(OAc)2 were mixed and heated at 80deg Celsius. Polymerization was monitored using UV-Vis spectroscopy and SEC chromatography. Later to the reaction mixture, a capping agent (selected from G1) containing appropriate functional group was added and 3 hours later the second capping agent (selected from G2) added. After the reaction the crude reaction mixture was evaporated off and passed through a gel filtration column to remove small organic molecules and low MW oligomers. Later the crude polymer passed through a Tangential flow filtration system equipped with a 100K MWCO membrane. It is washed using 20% ethanol until the absorption of the filtrate diminishes.

Method 2: Alternatively, the polymerization can be done by self-polymerizing a bromo-boronic ester of DHP molecule. In a round bottom flask DHP bromoboronic ester was taken in (DMF-water) mixture and purged with nitrogen for 10 minutes. Under nitrogen about 10 equivalent of CsF and 5% of Pd(OAc)$_2$ were mixed and heated at 80deg Celsius. Polymerization was monitored using UV-Vis spectroscopy and SEC chromatography. Later to the reaction mixture, a capping agent (selected from G1) containing appropriate functional group was added and 3 hours later the second capping agent (selected from G2) added. After the reaction the crude reaction mixture was evaporated off and passed through a gel filtration column to remove small organic molecules and low MW oligomers. Later the crude polymer passed through a Tangential flow filtration system equipped with a 100K MWCO membrane. It is washed using 20% ethanol until the absorption of the filtrate diminishes.

Method 3: In a round bottom flask both the dibromo dihydrophenanthrene and diboronic dihydrophanenthrene monomers (1:1) were taken and dissolved in THF-water (4:1) mixture containing 10 equivalent of $K_2CO_3$ and 3% Pd(PPh$_3$)$_4$. The reaction mixture was put on a Schlenk line and was degassed with three freeze-pump-thaw cycles and then heated to 80deg C. under nitrogen with vigorous stirring for 18 hours. Later to the reaction mixture, a capping agent (selected from G1) containing appropriate functional group was added via a cannula under excess nitrogen pressure and 3 hours later the second capping agent (selected from G2) added. After the reaction the crude reaction mixture was evaporated off and passed through a gel filtration column to remove small organic molecules and low MW oligomers. Later the crude polymer passed through a Tangential flow filtration system equipped with a 100K MWCO membrane. It is washed using 20% ethanol until the absorption of the filtrate diminishes.

Method 4: Alternatively the polymerization can be done by self-polymerizing a bromo-boronic ester of dihydrophenanthrene molecule. In a round bottom flask dihydrophenanthrene bromoboronic ester was taken and dissolved in THF-water (4:1) mixture containing 10 equivalent of $K_2CO_3$ and 3% Pd(PPh$_3$)$_4$. The reaction mixture was put on a Schlenk line and was degassed with three freeze-pump-thaw cycles and then heated to 80deg C. under nitrogen with vigorous stirring for 18 hours. Later to the reaction mixture, a capping agent (selected from G1) containing appropriate functional group was added via a cannula under excess nitrogen pressure and 3 hours later the second capping agent (selected from G2) added. After the reaction the crude reaction mixture was evaporated off and passed through a gel filtration column to remove small organic molecules and low MW oligomers. Later the crude polymer passed through a Tangential flow filtration system equipped with a 100K MWCO membrane. It is washed using 20% ethanol until the absorption of the filtrate diminishes.

Example 2: Preparation of Fluorene-DHP Copolymer Complex

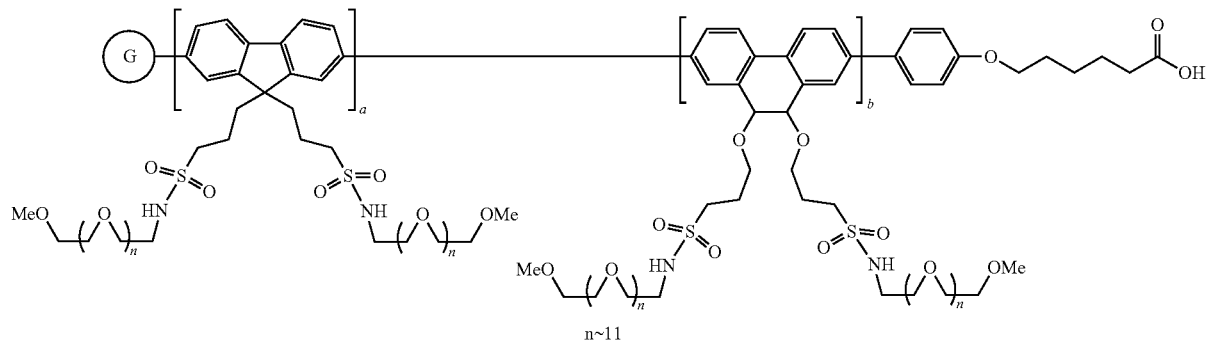

Method 1: In a round bottom flask both the dibromo DHP and diboronic fluorene monomers (1:1) were taken in (DMF-water) mixture and purged with nitrogen for 10 minutes. Under nitrogen about 20 equivalent of CsF and 10% of Pd(OAc)2 were mixed and heated at 80deg Celsius. Polymerization was monitored using UV-Vis spectroscopy and SEC chromatography. Later to the reaction mixture, a capping agent (selected from G1) containing appropriate functional group was added and 3 hours later the second capping agent (selected from G2) added. After the reaction the crude reaction mixture was evaporated off and passed through a gel filtration column to remove small organic molecules and low MW oligomers. Later the crude polymer passed through a Tangential flow filtration system equipped with a 100K MWCO membrane. It is washed using 20% ethanol until the absorption of the filtrate diminishes.

Method 2: In a round bottom flask both the dibromo fluorene and diboronic DHP monomers (1:1) were taken in (DMF-water) mixture and purged with nitrogen for 10 minutes. Under nitrogen about 20 equivalent of CsF and 10% of Pd(OAc)2 were mixed and heated at 80deg celcius. Polymerization was monitored using UV-Vis spectroscopy and SEC chromatography. Later to the reaction mixture, a capping agent (selected from G1) containing appropriate functional group was added and 3 hours later the second capping agent (selected from G2) added. After the reaction the crude reaction mixture was evaporated off and passed through a gel filtration column to remove small organic molecules and low MW oligomers. Later the crude polymer passed through a Tangential flow filtration system equipped with a 100K MWCO membrane. It is washed using 20% ethanol until the absorption of the filtrate diminishes.

Method 3: In a round bottom flask both the dibromo dihydrophenanthrene and diboronic fluorene monomers (1:1) were taken and dissolved in THF-water (4:1) mixture containing 10 equivalent of $K_2CO_3$ and 3% $Pd(PPh_3)_4$. The reaction mixture was put on a Schlenk line and was degassed with three freeze-pump-thaw cycles and then heated to 80deg C. under nitrogen with vigorous stirring for 18 hours. Later to the reaction mixture, a capping agent (selected from G1) containing appropriate functional group was added via a cannula under excess nitrogen pressure and 3 hours later the second capping agent (selected from G2) added. After the reaction the crude reaction mixture was evaporated off and passed through a gel filtration column to remove small organic molecules and low MW oligomers. Later the crude polymer passed through a Tangential flow filtration system equipped with a 100K MWCO membrane. It is washed using 20% ethanol until the absorption of the filtrate diminishes.

Method 4: In a round bottom flask dibromo fluorene and diboronic dihydrophenanthrene monomers (1:1) were taken and dissolved in THF-water (4:1) mixture containing 10 equivalent of $K_2CO_3$ and 3% Pd(PPh3)4. The reaction mixture was put on a Schlenk line and was degassed with three freeze-pump-thaw cycles and then heated to 80deg C. under nitrogen with vigorous stirring for 18 hours. Later to the reaction mixture, a capping agent (selected from G1) containing appropriate functional group was added via a cannula under excess nitrogen pressure and 3 hours later the second capping agent (selected from G2) added. After the reaction the crude reaction mixture was evaporated off and passed through a gel filtration column to remove small organic molecules and low MW oligomers. Later the crude polymer passed through a Tangential flow filtration system equipped with a 100K MWCO membrane. It is washed using 20% ethanol until the absorption of the filtrate diminishes.

Example 3 Comparison of Fluorescence Emission Spectra

Comparison of fluorescence emission spectra of fluorene (Fl-Fl), dihydrophenanthrene (DHP-DHP) and fluorene-DHP (DHP-Fl) polymers were undertaken. DHP containing polymers show a marked difference in their fluorescence maxima which is at 426-428 nm, whereas the fluorene based polymers show a maxima of 421 nm (FIG. 1).

Example 4 Comparison of Absorption Spectra

Figure 2:
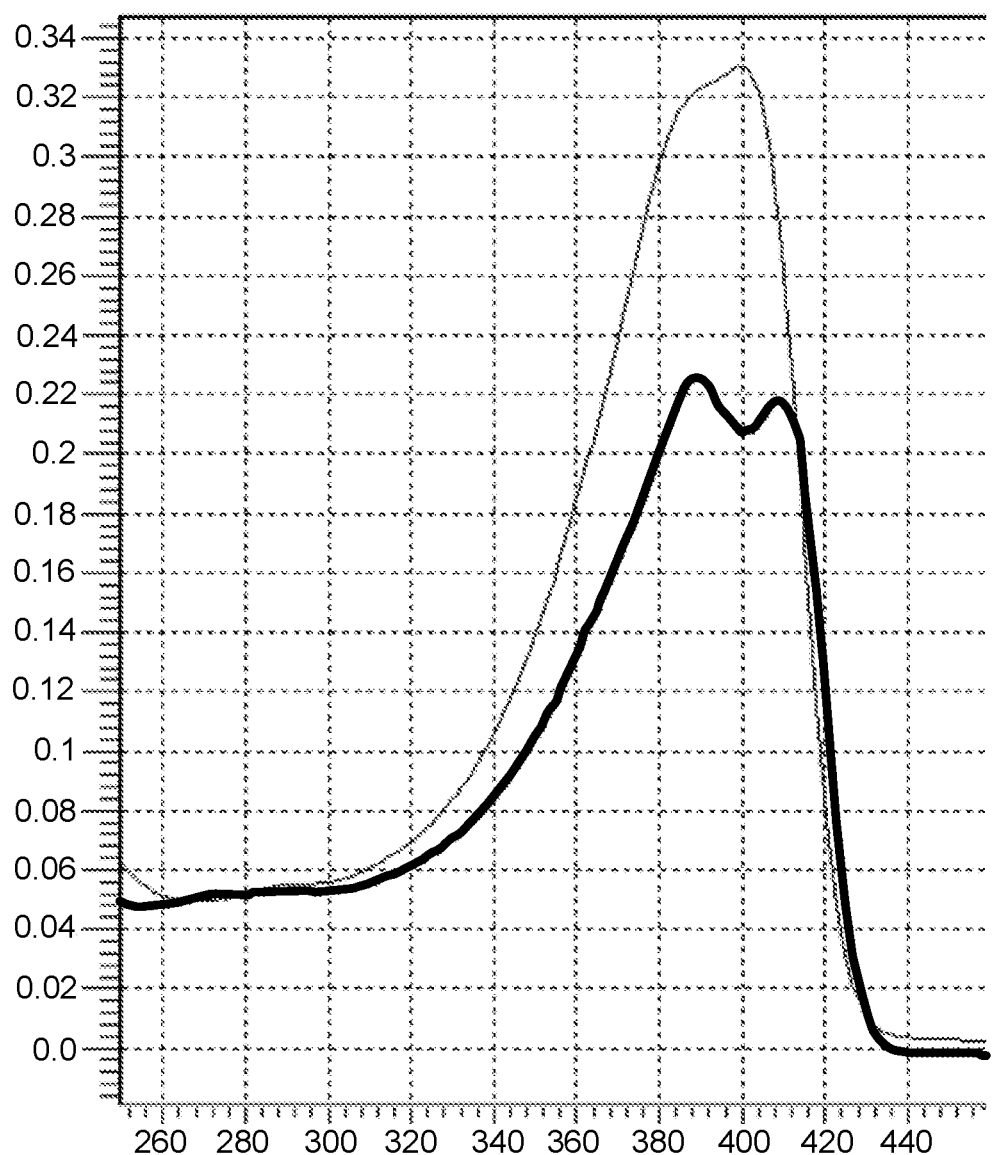
FIG. 2 shows the absorption spectra of both FF polymer and DD polymer. The graph shows absorption of the DD polymer (black curve) at 390 and 410 nm, whereas the FF (grey curve) polymer shows the maxima around 401 nm. Samples were measured under different concentration.

The absorption spectra of both fluorene (Fl-Fl) polymer and dihydrophenanthrene (DHP-DHP) polymer were measured. The graph shows absorption of the DHP-DHP polymer (black curve) at 390 and 410 nm, whereas the Fl-Fl (grey curve) polymer shows the maxima around 400 nm. Samples were measured under different concentration (FIG. 2).

Example 5 CD4 Signal to Noise Ratio

Figure 3:
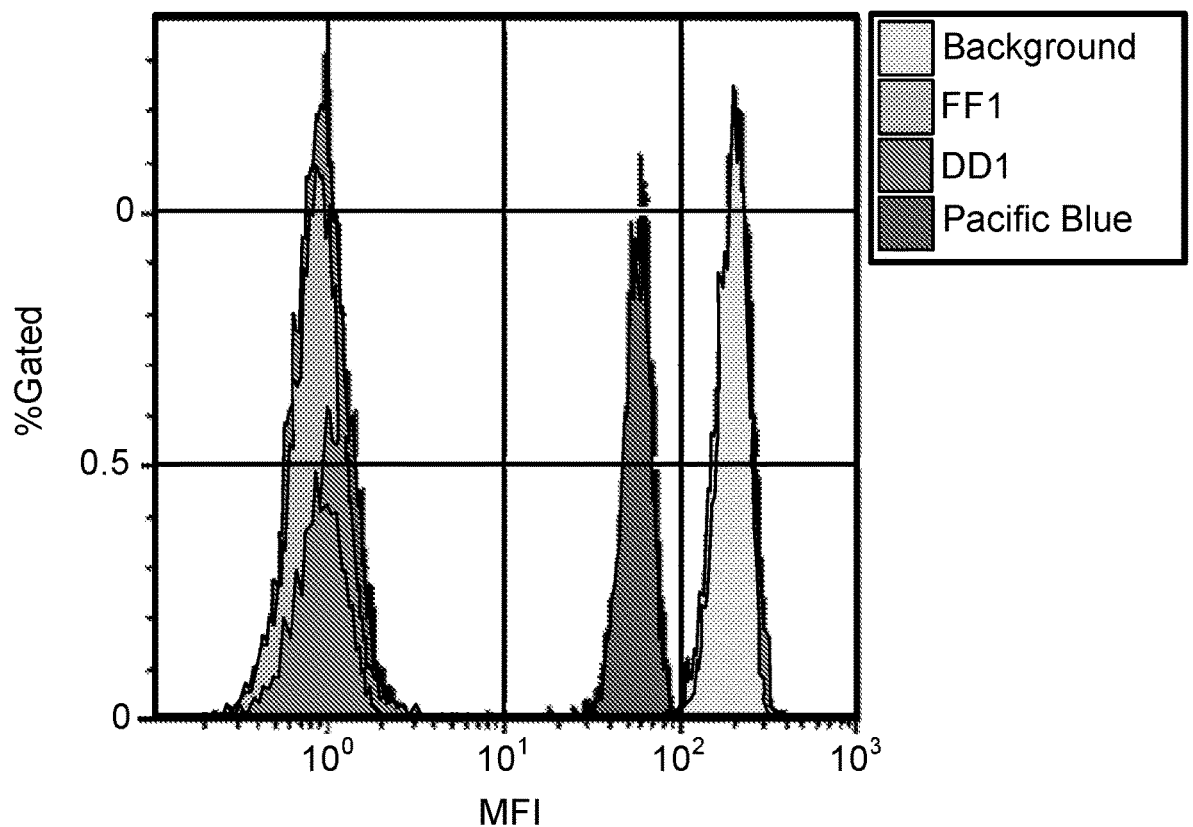
FIG. 3 shows the flow cytometric analysis of lysed whole blood stained with the new polymers-labeled anti-human CD4 and Pacific Blue-labeled CD4. The positive signal intensity of polymer dyes were nearly 5 times higher than Pacific Blue.

The flow cytometric analysis of lysed whole blood stained with the new polymers-labeled anti-human CD4 and Pacific Blue-labeled CD4 was undertaken. The positive signal intensity of polymer dyes were nearly 5 times higher than Pacific Blue (FIG. 3).

Example 6

Polymers of the present invention were found to possess certain physical and chemical characteristics of absorption, fluorescence, brightness, molecular weight, polydispersity, dye to protein ratio when conjugated to an antibody etc. The preferred ranges of these parameters are shown in the table of FIG. 4.

Figure 5:
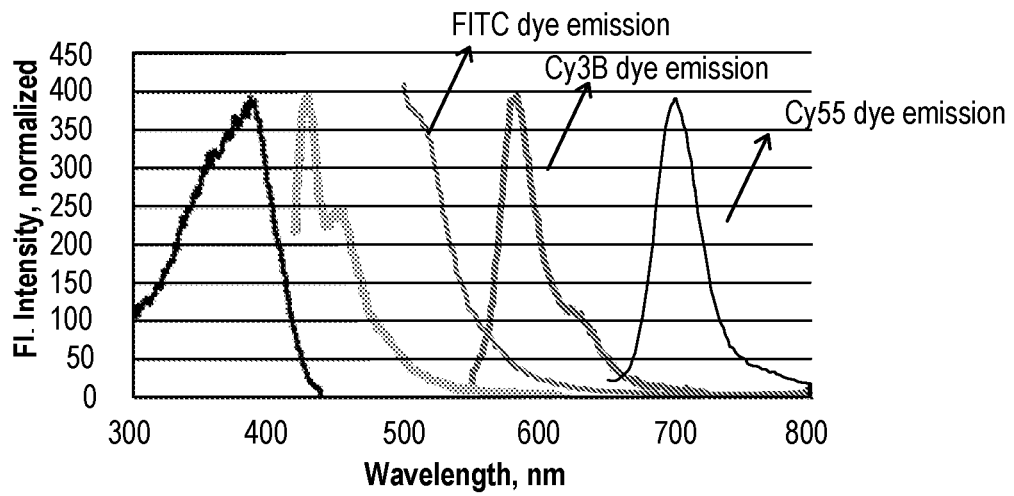
FIG. 5 shows the excitation and emission spectra of tandem polymers. Excitation was carried out at the polymer maxima (405 nm) and the emissions observed from the various acceptor dyes attached to the backbone. Dye 1—FITC, Dye 2—Cy3B, Dye 3—Cy55.
Figure 5:
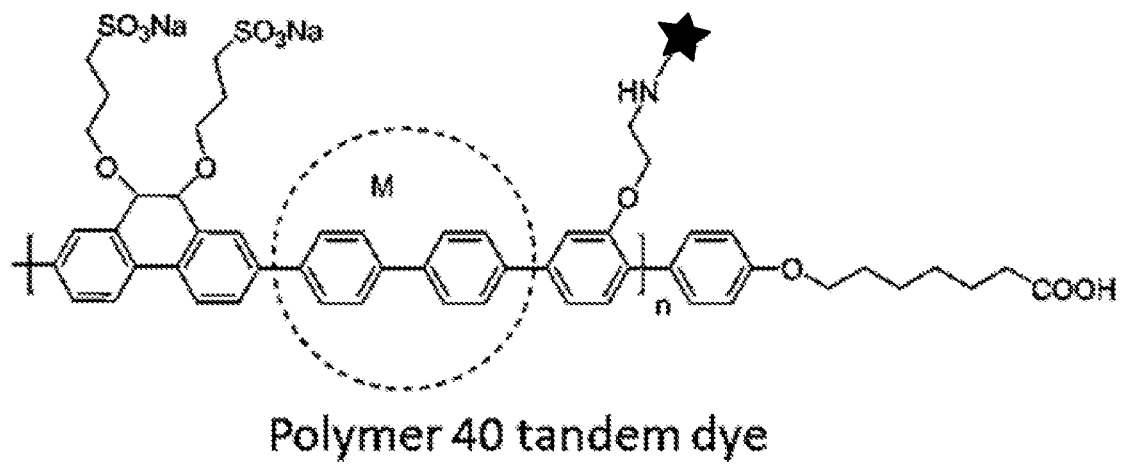

The excitation and emission spectra of tandem polymers was measured. Excitation was carried out at the polymer maxima (405 nm) and the emissions observed from the various acceptor dyes attached to the backbone (FIG. 5).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:
1. A water soluble fluorescent polymer having the structure of Formula II:

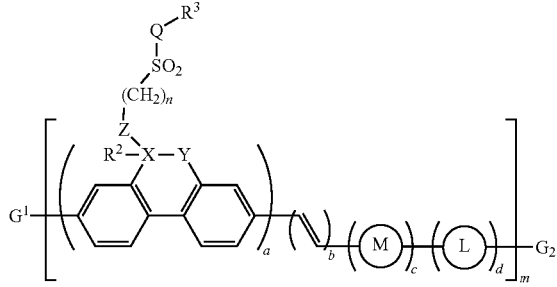

(II)

wherein;
each X is independently selected from the group consisting of a C and Si;
each Y is independently selected from the group consisting of a bond, $CR^1R^2$, and $SiR^1R^2$;
when Y is a bond X is directly bonded to both rings;
each $R^1$ is independently selected from the group consisting of polyethylene glycol (PEG), ammonium alkyl salt, ammonium alkyloxy salt, ammonium oligoether salt, sulfonate alkyl salt, sulfonate alkoxy salt, sulfonate oligoether salt, sulfonamido oligoether, and

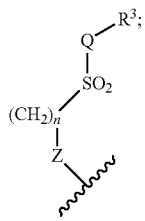

each $R^2$ is independently selected from the group consisting of H, alkyl, alkene, alkyne, cycloalkyl, haloalkyl, alkoxy, (hetero)aryloxy, aryl, (hetero)arylamino, a PEG group, ammonium alkyl salt, ammonium alkyloxy salt, ammonium oligoether salt, sulfonate alkyl salt, sulfonate alkoxy salt, sulfonate oligoether salt, sulfonamido oligoether, and

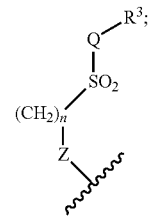

each $R^3$ is independently selected from the group consisting of H, alkyl, alkene, alkyne, cycloalkyl, haloalkyl, alkoxy, (hetero)aryloxy, aryl, (hetero)arylamino, and a PEG group;
each Z is independently selected from the group consisting of C, O, and N;
each Q is independently selected from the group consisting of a bond, NH, $NR^4$, and $CH_2$;
each M is independently an electron rich linker unit capable of altering the polymer band gap and is evenly or randomly distributed along the polymer main chain and is each independently selected from the group consisting of

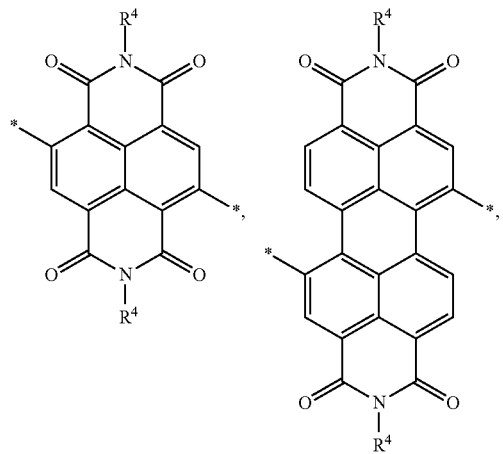

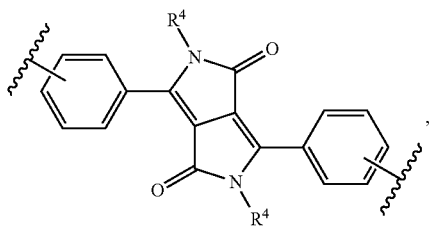

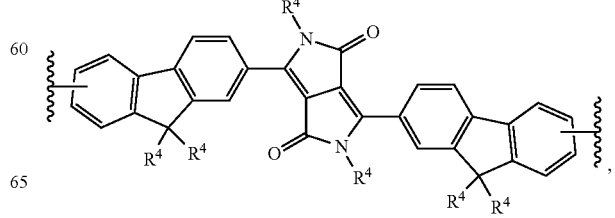

-continued

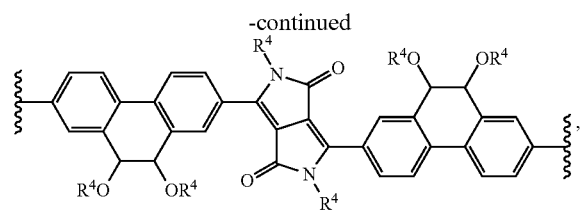

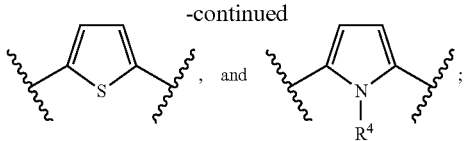, and

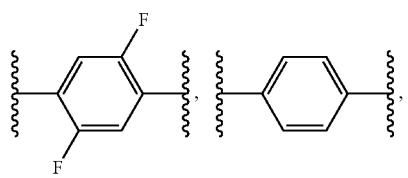

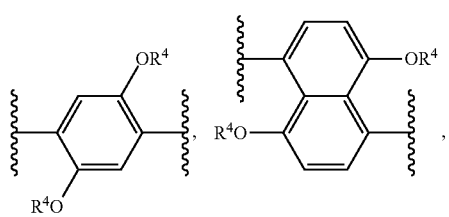

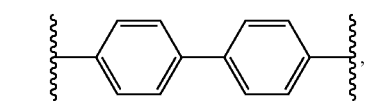

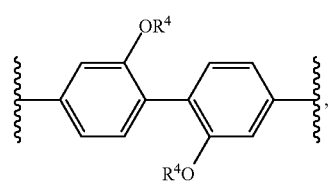

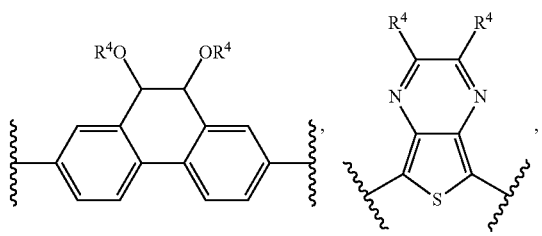

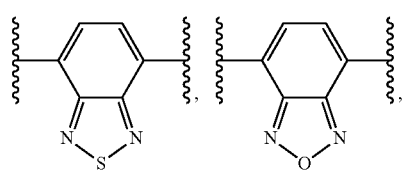

wherein, each $R^4$ is a non-ionic side group capable of imparting solubility in water in excess if 10 mg/mL and is each independently selected from the group consisting of halogen, hydroxyl, $C_1$-$C_{12}$ alkyl, $C_2$-$C_{12}$ alkene, $C_2$-$C_{12}$ alkyne, $C_3$-$C_{12}$ cycloalkyl, $C_1$-$C_{12}$ haloalkyl, $C_1$-$C_{12}$ alkoxy, $C_2$-$C_{18}$ (hetero)aryloxy, $C_2$-$C_{18}$ (hetero)arylamino, $(CH_2)_{x'}(OCH_2-CH_2)_{y'}OCH_3$ where each x' is independently an integer from 0-20; each y' is independently an integer from 0-50, and a $C_2$-$C_{18}$ (hetero)aryl group;

each optional linker L is an aryl or hetroaryl group evenly or randomly distributed along the polymer main chain and are substituted with one or more pendant chains terminated with a functional group selected from the group consisting of amine, carbamate, carboxylic acid, carboxylate, maleimide, activated ester, N-hydroxysuccinimidyl, hydrazine, hydrazide, hydrazone, azide, alkyne, aldehyde, thiol, and protected groups thereof for conjugation to another substrate, acceptor dye, molecule or binding agent;

$G^1$ and $G^2$ are each independently selected from the group consisting of hydrogen, halogen, alkyne, optionally substituted aryl, optionally substituted heteroaryl, halogen substituted aryl, silyl, diazonium salt, triflate, acetyloxy, azide, sulfonate, phosphate, boronic acid substituted aryl, boronic ester substituted aryl, boronic ester, boronic acid, optionally substituted dihydrophenanthrene (DHP), optionally substituted fluorene, aryl or hetroaryl substituted with one or more pendant chains terminated with a functional group selected from amine, carbamate, carboxylic acid, carboxylate, maleimide, activated ester, N-hydroxysuccinimidyl, hydrazine, hydrazide, hydrazone, azide, alkyne, aldehyde, thiol, and protected groups thereof for conjugation to a substrate, or a binding agent;

a, c, and d define the mol % of each unit within the structure which each can be evenly or randomly repeated and where a is a mol % from 10 to 100%, c is a mol % from 0 to 90%, and each d is a mol % from 0 to 25%;

each b is independently 0 or 1;
m is an integer from 1 to about 10,000; and
each n is independently an integer from 1 to 20.

2. The polymer of claim 1, wherein the polymer has the structure of Formula III:

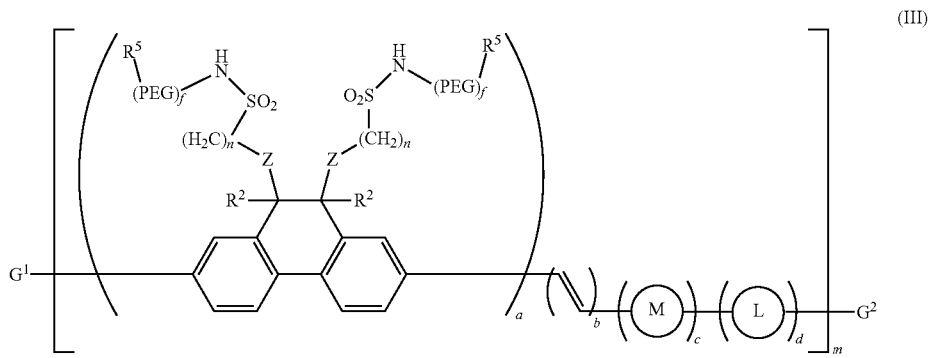

wherein,
each f is independently an integer from 0 to 50 and each $R^5$ is independently selected from the group consisting of H, $C_1$-$C_{12}$ alkyl, $C_2$-$C_{12}$ alkene, $C_2$-$C_{12}$ alkyne, $C_3$-$C_{12}$ cycloalkyl, $C_1$-$C_{12}$ haloalkyl, $C_1$-$C_{12}$ alkoxy, $C_2$-$C_{18}$ (hetero)aryloxy, $C_2$-$C_{18}$ (hetero)arylamino, and $C_1$-$C_{12}$ alkoxy.

3. The polymer of claim 2, wherein the polymer has the structure of Formula IV:

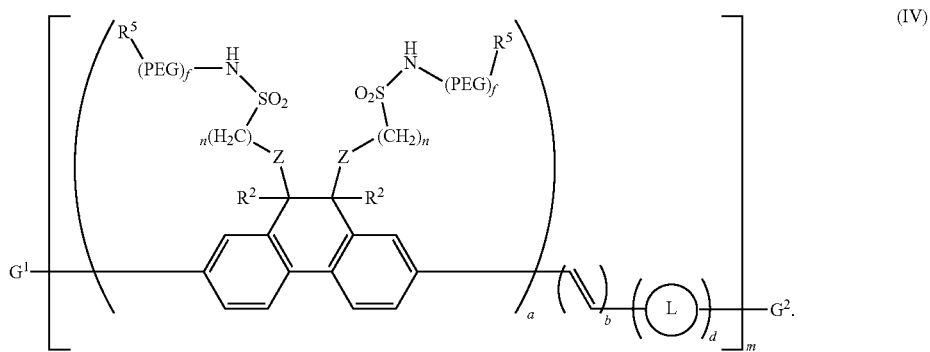

4. The polymer of claim 1, wherein the polymer has the structure of Formula V:

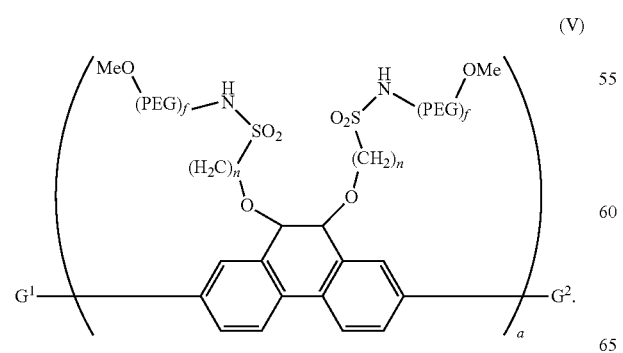

5. The polymer of claim 1, wherein the polymer is a copolymer and has the structure of Formula VI:

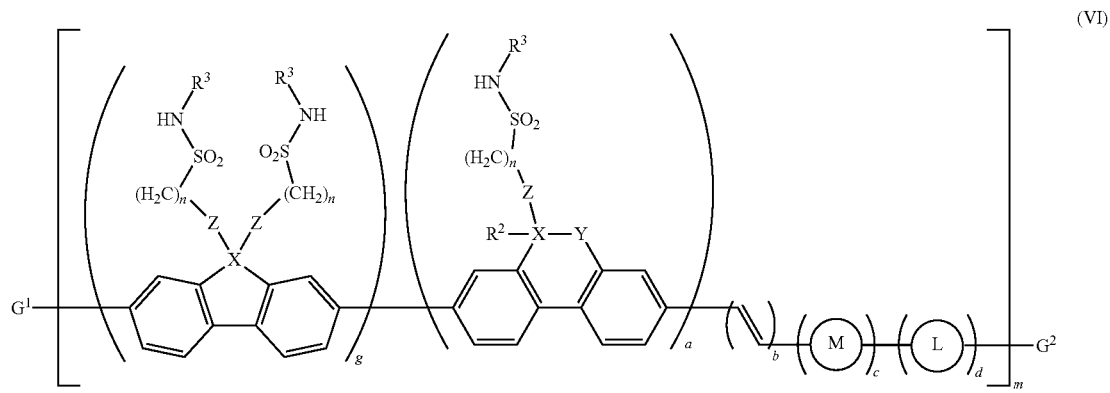

(VI)

wherein g and a together is a mol % from 10 to 100%.

6. The polymer of claim 1, wherein the polymer is a copolymer and has the structure of Formula VII:

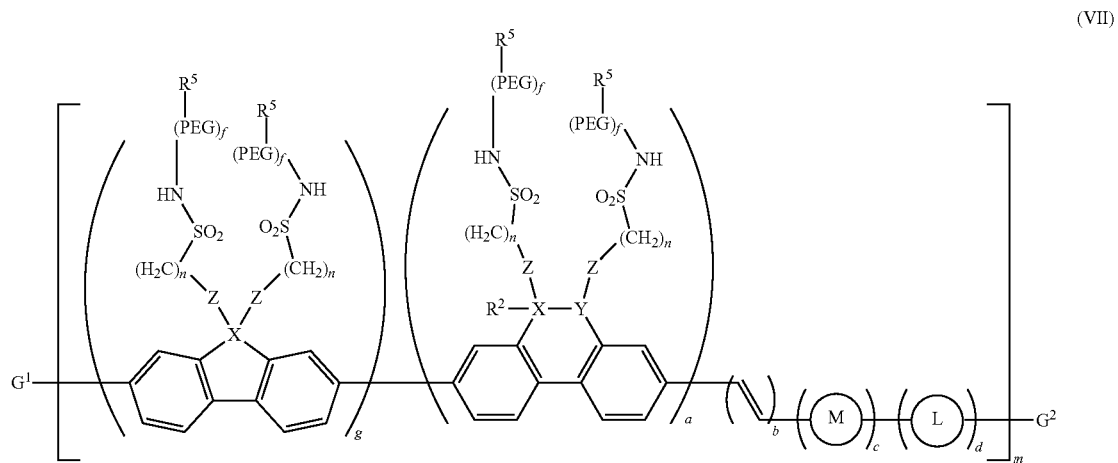

(VII)

wherein,
each g and a together is a mol % from 10 to 100%; and
each f is independently an integer from 0 to 50 and each $R^5$ is independently selected from the group consisting of H, $C_1$-$C_{12}$ alkyl, $C_2$-$C_{12}$ alkene, $C_2$-$C_{12}$ alkyne, $C_3$-$C_{12}$ cycloalkyl, $C_1$-$C_{12}$ haloalkyl, $C_1$-$C_{12}$ alkoxy, $C_2$-$C_{18}$ (hetero)aryloxy, $C_2$-$C_{18}$ (hetero)arylamino, and $C_1$-$C_{12}$ alkoxy.

7. The polymer of claim 6, wherein the polymer is a copolymer and has the structure of Formula VIII:
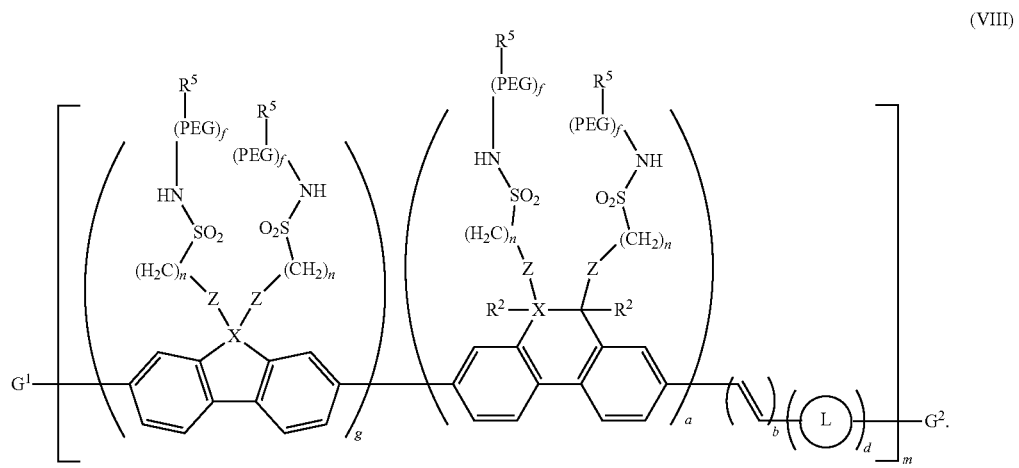
(VIII)
8. The polymer of claim 6, wherein the polymer is a copolymer and has the structure of Formula IX:
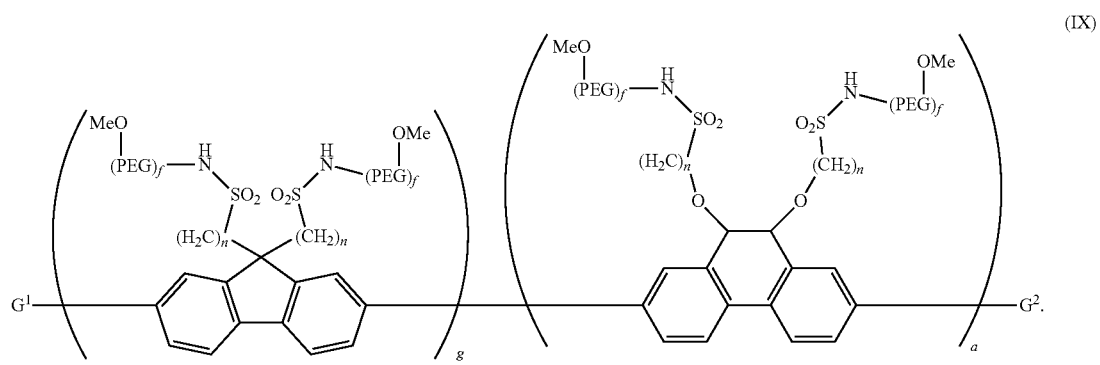
(IX)
9. The polymer of claim 1 wherein L is each independently selected from the group consisting of
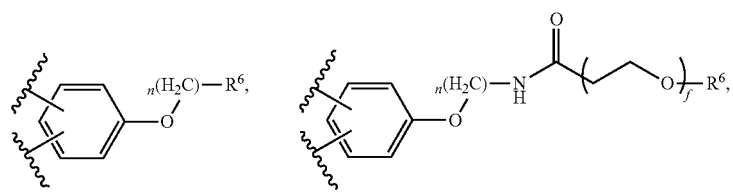
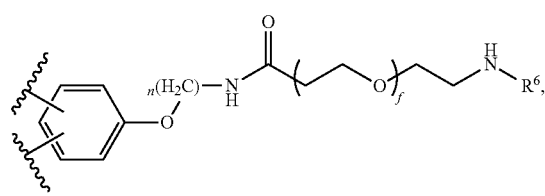

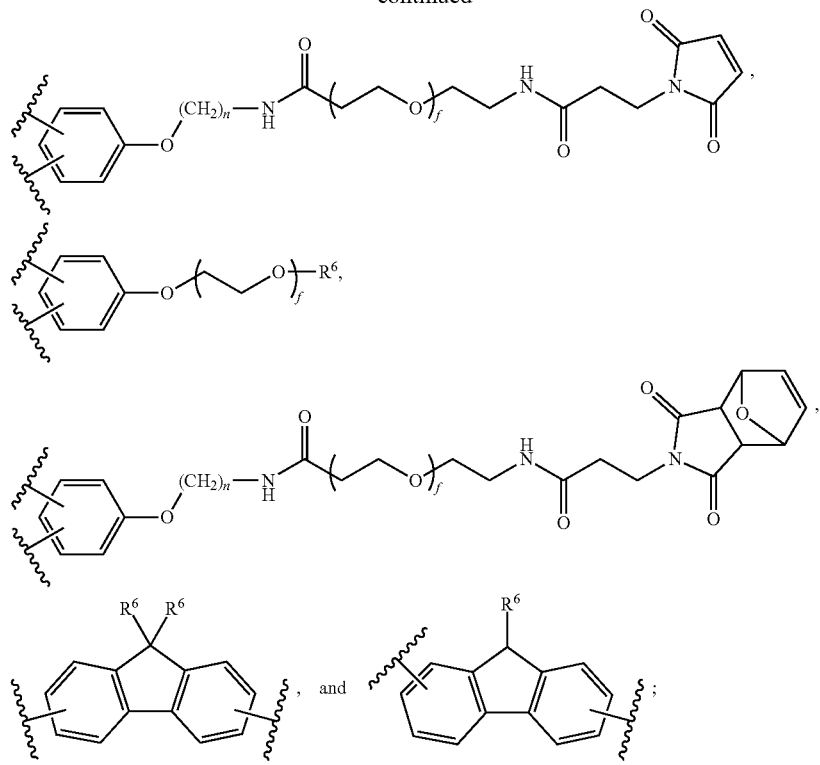

wherein, each $R^6$ is independently selected from the group consisting of H, OH, SH, NHCOO-t-butyl, $(CH_2)_n COOH$, $(CH_2)_n COOCH_3$, $(CH_2)_n NH_2$, $(CH_2)_n NH—(CH_2)_n—CH_3$, $(CH_2)_n NHCOOH$, $(CH_2)_n NHCO—(CH_2)_n—CO—(CH_2)_n—CH_3$, $(CH_2)_n NHCOO—(CH_2)_n—CH_3$, $(CH_2)_n NHCOOC(CH_3)_3$, $(CH_2)_n NHCO(C_3-C_{12})$cycloalkyl, $(CH_2)_n NHCO(CH_2CH_2O)_f$, $(CH_2)_n NHCO(CH_2)_n COOH$, $(CH_2)_n NHCO(CH_2)_n COO(CH_2)_n CH_3$, $(CH_2)_n(OCH_2CH_2)_f OCH_3$, N-maleimide, halogen, $C_2-C_{12}$ alkene, $C_2-C_{12}$ alkyne, $C_3-C_{12}$ cycloalkyl, $C_1-C_{12}$ halo alkyl, $C_1-C_{12}$ (hetero)aryl, $C_1-C_{12}$ (hetero)arylamino, and benzyl optionally substituted with one or more halogen, hydroxyl, $C_1-C_{12}$ alkoxy, or $(OCH_2CH_2)_f OCH_3$;

each f is independently an integer from 0 to 50; and each n is independently an integer from 1 to 20.

10. The polymer of claim 1, wherein $G^1$ and $G^2$ are each independently selected from the group consisting of optionally substituted dihydrophenanthrene (DHP), optionally substituted fluorene, aryl substituted with one or more pendant chains terminated with a functional group, and a hetroaryl substituted with one or more pendant chains terminated with a functional group.

11. The polymer of claim 1, wherein $G^1$ and $G^2$ are each independently selected from the group consisting of

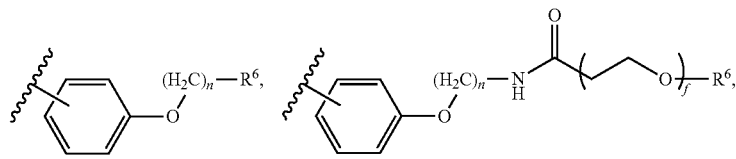

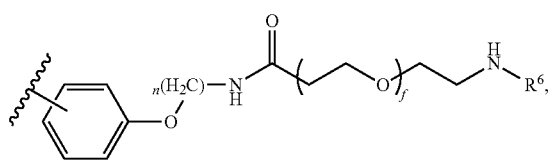

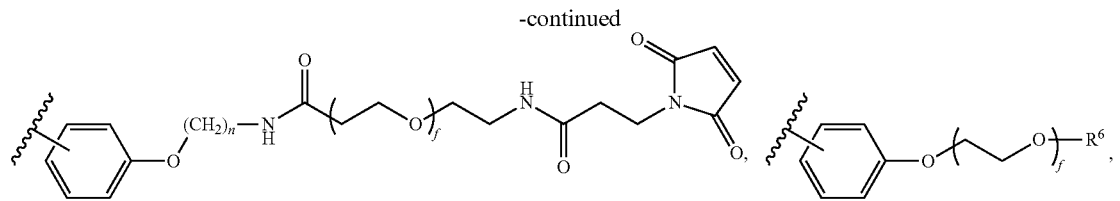

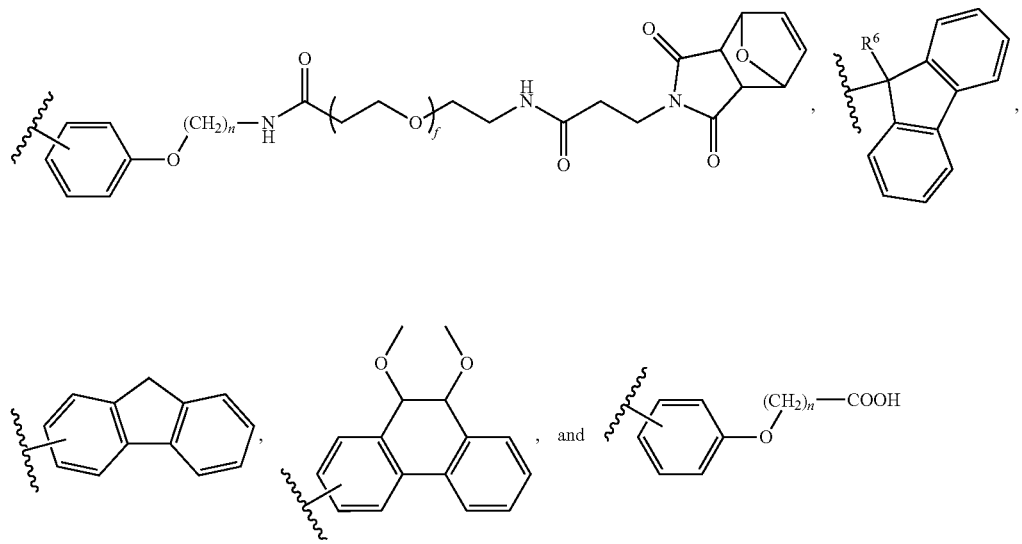

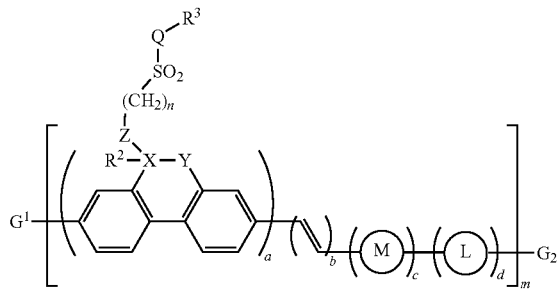

wherein, each $R^6$ is independently selected from the group consisting of H, OH, SH, NHCOO-t-butyl, $(CH_2)_n COOH$, $(CH_2)_n COOCH_3$, $(CH_2)_n NH_2$, $(CH_2)_n NH—(CH_2)_n—CH_3$, $(CH_2)_n NHCOOH$, $(CH_2)_n NHCO—(CH_2)_n—CO—(CH_2)_n—CH_3$, $(CH_2)_n NHCOO—(CH_2)_n—CH_3$, $(CH_2)_n NHCOOC(CH_3)_3$, $(CH_2)_n NHCO(C_3-C_{12})$cycloalkyl, $(CH_2)_n NHCO(CH_2CH_2O)_f$, $(CH_2)_n NHCO(CH_2)_n COOH$, $(CH_2)_n NHCO(CH_2)_n COO(CH_2)_n CH_3$, $(CH_2)_n (OCH_2CH_2)_f OCH_3$, N-maleimide, halogen, $C_2-C_{12}$ alkene, $C_2-C_{12}$ alkyne, $C_3-C_{12}$ cycloalkyl, $C_1-C_{12}$ halo alkyl, $C_1-C_{12}$ (hetero)aryl, $C_1-C_{12}$ (hetero)arylamino, and benzyl optionally substituted with one or more halogen, hydroxyl, $C_1-C_{12}$ alkoxy, or $(OCH_2CH_2)_f OCH_3$;

each f is independently an integer from 0 to 50; and each n is independently an integer from 1 to 20.

12. The polymer of claim 1, further comprising a binding agent linked to said polymer.

13. The polymer of claim 12, wherein the binding agent is an antibody.

14. A method for detecting an analyte in a sample comprising:

providing a sample that is suspected of containing the analyte;

contacting the sample with a binding agent conjugated to a water soluble polymer having the structure of Formula II:

(II)

wherein;

each X is independently selected from the group consisting of a C and Si;

each Y is independently selected from the group consisting of a bond, $CR_1R^2$, and $SiR^1R^2$;

when Y is a bond X is directly bonded to both rings;

each $R^1$ is independently selected from the group consisting of PEG, ammonium alkyl salt, ammonium alkyloxy salt, ammonium oligoether salt, sulfonate alkyl salt, sulfonate alkoxy salt, sulfonate oligoether salt, sulfonamido oligoether, and

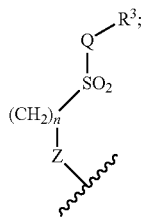

each R² is independently selected from the group consisting of H, alkyl, alkene, alkyne, cycloalkyl, haloalkyl, alkoxy, (hetero)aryloxy, aryl, (hetero)arylamino, a PEG group, ammonium alkyl salt, ammonium alkyloxy salt, ammonium oligoether salt, sulfonate alkyl salt, sulfonate alkoxy salt, sulfonate oligoether salt, sulfonamido oligoether, and

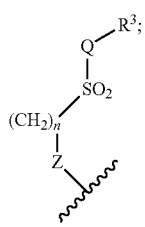

each R³ is independently selected from the group consisting of H, alkyl, alkene, alkyne, cycloalkyl, haloalkyl, alkoxy, (hetero)aryloxy, aryl, (hetero)arylamino, and a PEG group;

each Z is independently selected from the group consisting of C, O, and N;

each Q is independently selected from the group consisting of a bond, NH, NR⁴, and CH₂;

each M is independently an electron rich linker unit capable of altering the polymer band gap and is evenly or randomly distributed along the polymer main chain and is each independently selected from the group consisting of

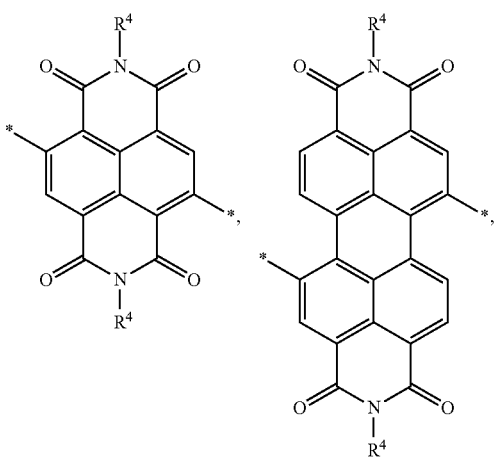

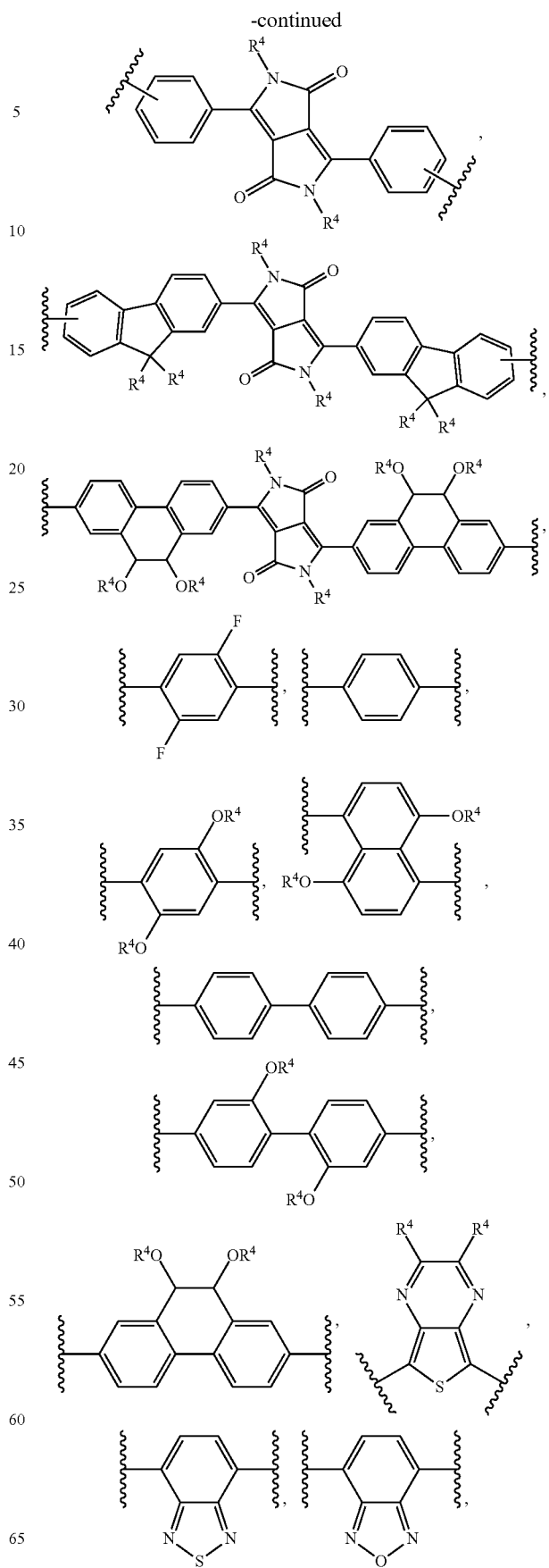

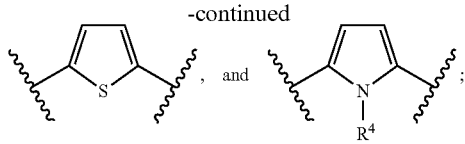

wherein, each $R^4$ is a non-ionic side group capable of imparting solubility in water in excess if 10 mg/mL and is each independently selected from the group consisting of halogen, hydroxyl, $C_1$-$C_{12}$ alkyl, $C_2$-$C_{12}$ alkene, $C_2$-$C_{12}$ alkyne, $C_3$-$C_{12}$ cycloalkyl, $C_1$-$C_{12}$ haloalkyl, $C_1$-$C_{12}$ alkoxy, $C_2$-$C_{18}$ (hetero)aryloxy, $C_2$-$C_{18}$ (hetero)arylamino, $(CH_2)_{x'}(OCH_2-CH_2)_{y'}OCH_3$ where each x' is independently an integer from 0-20; each y' is independently an integer from 0-50, and a $C_2$-$C_{18}$ (hetero)aryl group, each optional linker L is an aryl or hetroaryl group evenly or randomly distributed along the polymer main chain and are substituted with one or more pendant chains terminated with a functional group selected from the group consisting of amine, carbamate, carboxylic acid, carboxylate, maleimide, activated ester, N-hydroxysuccinimidyl, hydrazine, hydrazid, hydrazone, azide, alkyne, aldehyde, thiol, and protected groups thereof for conjugation to another substrate, acceptor dye, molecule or binding agent;

$G^1$ and $G^2$ are each independently selected from the group consisting of hydrogen, halogen, alkyne, optionally substituted aryl, optionally substituted heteroaryl, halogen substituted aryl, silyl, diazonium salt, triflate, acetyloxy, azide, sulfonate, phosphate, boronic acid substituted aryl, boronic ester substituted aryl, boronic ester, boronic acid, optionally substituted dihydrophenanthrene (DHP), optionally substituted fluorene, aryl or hetroaryl substituted with one or more pendant chains terminated with a functional group selected from amine, carbamate, carboxylic acid, carboxylate, maleimide, activated ester, N-hydroxysuccinimidyl, hydrazine, hydrazide, hydrazone, azide, alkyne, aldehyde, thiol, and protected groups thereof for conjugation to a substrate or binding agent;

a, c, and d define the mol % of each unit within the structure which each can be evenly or randomly repeated and where a is a mol % from 10 to 100%, c is a mol % from 0 to 90%, and each d is a mol % from 0 to 25%;

each b is independently 0 or 1;

m is an integer from 1 to about 10,000; and each n is independently an integer from 1 to 20; and wherein the binding agent is capable of interacting with the analyte or a target-associated biomolecule.

15. The method of claim 14, wherein the binding agent is a protein, peptide, affinity ligand, antibody, antibody fragment, sugar, lipid, nucleic acid or an aptamer.

16. The method of claim 14, wherein the binding agent is an antibody.

17. The method of claim 16, wherein the method is configured for flow cytometry.

18. The method of claim 16, wherein the binding agent is bound to a substrate.

19. The method of claim 16, wherein the analyte is a protein expressed on a cell surface.

20. The method of claim 16, wherein the method is configured as an immunoassay.

21. The assay method of claim 16, wherein the method further comprises providing additional binding agents for detecting additional analytes simultaneously.

22. The compound of claim 1, wherein each $R^3$ is independently selected from the group consisting of alkyl, alkene, alkyne, cycloalkyl, haloalkyl, alkoxy, (hetero)aryloxy, aryl, (hetero)arylamino, and a PEG group.

* * * * *